(12) United States Patent
Knill et al.

(10) Patent No.: US 12,246,007 B2
(45) Date of Patent: Mar. 11, 2025

(54) LIQUID BENDAMUSTINE PHARMACEUTICAL COMPOSITIONS

(71) Applicant: HOSPIRA AUSTRALIA PTY LTD, Sydney (AU)

(72) Inventors: Andrew Malcolm Knill, Sydney (AU); Noel Norris, Sydney (AU)

(73) Assignee: HOSPIRA AUSTRALIA PTY LTD, Sydney (AU)

( * ) Notice: Subject to any disclaimer, the term of this patent is extended or adjusted under 35 U.S.C. 154(b) by 648 days.

(21) Appl. No.: 17/268,780

(22) PCT Filed: Aug. 14, 2019

(86) PCT No.: PCT/IB2019/056903
§ 371 (c)(1),
(2) Date: Feb. 16, 2021

(87) PCT Pub. No.: WO2020/035806
PCT Pub. Date: Feb. 20, 2020

(65) Prior Publication Data
US 2021/0275500 A1    Sep. 9, 2021

Related U.S. Application Data

(60) Provisional application No. 62/815,376, filed on Mar. 8, 2019, provisional application No. 62/723,725, filed on Aug. 28, 2018, provisional application No. 62/764,975, filed on Aug. 17, 2018.

(51) Int. Cl.
*A61K 31/4184* (2006.01)
*A61K 9/00* (2006.01)
*A61K 47/10* (2017.01)

(52) U.S. Cl.
CPC ........ *A61K 31/4184* (2013.01); *A61K 9/0019* (2013.01); *A61K 47/10* (2013.01)

(58) Field of Classification Search
CPC .. A61K 31/4184; A61K 9/0019; A61K 47/10; A61K 9/08; A61P 35/00
See application file for complete search history.

(56) References Cited

U.S. PATENT DOCUMENTS

| | | |
|---|---|---|
| 8,344,006 B2 | 1/2013 | Drager et al. |
| 8,436,190 B2 | 5/2013 | Brittain et al. |
| 8,445,524 B2 | 5/2013 | Courvoisier et al. |
| 8,609,707 B2 | 12/2013 | Palepu et al. |
| 8,609,863 B2 | 12/2013 | Brittain et al. |
| 8,669,279 B2 | 3/2014 | Cooper et al. |
| 8,791,270 B2 | 7/2014 | Brittain et al. |
| 8,883,836 B2 | 11/2014 | Cooper et al. |
| 8,895,756 B2 | 11/2014 | Brittain et al. |
| 9,000,021 B2 | 4/2015 | Sundaram et al. |
| 9,034,908 B2 | 5/2015 | Sundaram |
| 9,144,568 B1 | 9/2015 | Sundaram |
| 9,265,831 B2 | 2/2016 | Palepu et al. |
| 9,533,955 B2 | 1/2017 | Cooper et al. |
| 9,572,796 B2 | 2/2017 | Palepu et al. |
| 9,572,797 B2 | 2/2017 | Palepu et al. |
| 9,572,887 B2 | 2/2017 | Sundaram |
| 9,579,384 B2 | 2/2017 | Sundaram et al. |
| 9,597,397 B2 | 3/2017 | Sundaram |
| 9,597,398 B2 | 3/2017 | Sundaram |
| 9,597,399 B2 | 3/2017 | Sundaram |
| 2011/0184036 A1* | 7/2011 | Palepu .................. A61K 47/18  514/394 |
| 2011/0190363 A1 | 8/2011 | Drager et al. |
| 2013/0210878 A1 | 8/2013 | Soppimath et al. |
| 2016/0158362 A1 | 6/2016 | Patel |
| 2018/0055823 A1* | 3/2018 | Patel ...................... A61P 35/00 |

FOREIGN PATENT DOCUMENTS

| | | | | |
|---|---|---|---|---|
| WO | WO-2015054550 A1 * | 4/2015 | ......... | A61K 31/4184 |
| WO | 2016/005995 | 1/2016 | | |
| WO | 2016/059590 A1 | 4/2016 | | |
| WO | 2017/175098 | 10/2017 | | |
| WO | WO-2017175098 A1 * | 10/2017 | ......... | A61K 31/4184 |

OTHER PUBLICATIONS

BENDEKA™ Prescribing Information, Feb. 2017, Reference ID: 4053871.
Kasa et al., "Stability-Indicating LC Method for the Estimation of Bendamustine Hydrochloride and its Related Impurities", Journal of Chromatographic Science, 2013, pp. 1-11.
Treanda® Prescribing Information, Oct. 2016, Reference ID: 4000389.
PCT/IB2019/056903 International Search Report, mailed Nov. 22, 2019.

\* cited by examiner

*Primary Examiner* — Matthew P Coughlin
*Assistant Examiner* — Ashli Ariana Chicks
(74) *Attorney, Agent, or Firm* — Jason G. Tebbutt

(57) ABSTRACT

Concentrated liquid pharmaceutical compositions comprising a) a pharmaceutically effective amount of bendamustine or a pharmaceutically acceptable salt thereof, b) a non-aqueous solvent, and c) at least about 2% water, suitable, after dilution, for administration to a mammal by injection are provided. The concentrated liquid pharmaceutical compositions can comprise a non-aqueous solvent comprising at least one organic polymeric compound solvent and at least one organic small molecule solvent. Methods of treating a cancer in a mammal in need of such treatment comprising administering to the mammal an effective amount of a concentrated liquid bendamustine pharmaceutical composition of the invention are also provided.

1 Claim, No Drawings

LIQUID BENDAMUSTINE PHARMACEUTICAL COMPOSITIONS

CROSS-REFERENCE TO RELATED APPLICATIONS

This application is a 371 of international application number PCT/IB2019/056903 filed Aug. 14, 2019, which claims priority to U.S. Provisional Patent Application No. 62/815,376 filed on Mar. 8, 2019 and U.S. Provisional Patent Application No. 62/723,725 filed on Aug. 28, 2018 and U.S. Provisional Patent Application No. 62/764,975 filed on Aug. 17, 2018. All applications to which priority is claimed are hereby incorporated by reference in their entirety for all purposes.

BACKGROUND

Bendamustine is indicated for treatment of certain cancers, for example chronic lymphocytic leukemia and non-Hodgkin's lymphoma. Bendamustine HCl (1H-benzimidazole-2-butanoic acid, 5-[bis(2-chloroethyl) amino]-1-methyl, monohydrochloride) is an alkylating agent with a structure including a benzimidazole ring, an active nitrogen mustard fragment and a residue of butanoic acid. The empirical molecular formula of bendamustine is $C_{16}H_{21}Cl_2N_3O_2$. (Kasa et al., Journal of Chromatographic Science 2013; 1-11). Bendamustine has the following chemical structure:

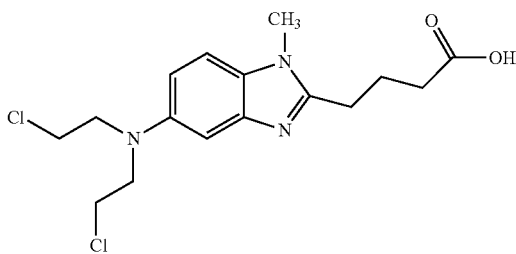 [SMILES: Cn1c(CCCC(=O)O)nc2cc(N(CCCl)CCCl)ccc21]

Bendamustine is the active pharmaceutical ingredient of several drugs approved by drug regulatory agencies. For example, the drug TREANDA® contains bendamustine hydrochloride as the active ingredient and was approved for marketing by the United States Food and Drug Administration (U.S. FDA) in 2008. TREANDA® is available as a solution (TREANDA® Injection) and a lyophilized powder (TREANDA® for Injection).

TREANDA® Injection is supplied as a sterile clear colorless to yellow non-aqueous solution in a single-dose vial at the concentration of 90 mg/mL of bendamustine HCl; each 0.5 mL vial of TREANDA® Injection contains 45 mg of bendamustine hydrochloride, 162 mg of propylene glycol, and 293 mg of N, N-dimethylacetamide (see, TREANDA U.S. FDA Label dated October 2016). U.S. Pat. No. 8,344,006 to Drager et al. relates to liquid pharmaceutical formulations comprising bendamustine or a bendamustine salt and a polar aprotic solvent; U.S. Pat. No. 8,344,006 (Drager et al.) state that polar aprotic solvents include molecules such as 1-methyl-2-pyrrolidone, 1,3-dimethyl-2-imidazolidinone, dimethylacetamide, dimethyl sulfoxide, acetone, tetrahydrofuran, 1,4-dioxane, acetonitrile, dimethyl formamide, and propylene carbonate. The pharmaceutical formulations of bendamustine or a bendamustine salt set forth in the claims of Drager et al. are indicated to be stable and non-aqueous liquids.

TREANDA® for Injection is supplied as a sterile non-pyrogenic white to off-white dry, lyophilized powder in a single-dose vial, each 25-mg vial thereof containing 25 mg of bendamustine hydrochloride and 42.5 mg of mannitol (Id.). Just prior to administration, TREANDA® for Injection is reconstituted with sterile water for injection, and the reconstituted solution must be transferred to the infusion bag within 30 minutes of reconstitution (Id.).

Both TREANDA® Injection and TREANDA® for Injection should be prepared for infusion as close as possible to the time of patient administration. Once diluted with an aqueous diluent, TREANDA® Injection is stable for 2 hours when stored at room temperature and room light; administration of diluted TREANDA® Injection must be completed within this time period (Id.). After reconstitution and dilution in a water-containing diluent, TREANDA® for Injection is stable for three hours when stored at room temperature and room light; administration of reconstituted and diluted TREANDA® for Injection must be completed within this period of time (Id.).

The drug BENDEKA™ also contains bendamustine hydrochloride as the active ingredient. BENDEKA™ was approved for marketing by the U.S. FDA in 2015. BENDEKA™ injection is supplied as a sterile, clear, and colorless to yellow ready-to-dilute solution in a multiple-dose clear glass vial. Each milliliter of BENDEKA™ injection contains 25 mg of bendamustine hydrochloride, 0.1 mL of propylene glycol, 5 mg of monothioglycerol, in polyethylene glycol 400. Sodium hydroxide may have been used in BENDEKA™ injection to adjust the acidity of polyethylene glycol 400. (See, BENDEKA U.S. FDA Label dated February 2017). BENDEKA™ is not indicated to contain water as an ingredient (Id.). U.S. Pat. No. 8,609,707 (Palepu et al.), entitled "Formulations of Bendamustine", relates to liquid bendamustine-containing compositions including (a) bendamustine or a pharmaceutically acceptable salt thereof; and (b) a fluid including (i) polyethylene glycol, propylene glycol or mixtures thereof; and (ii) a stabilizing amount of an antioxidant. Palepu et al. further state that, in several embodiments, the fluid is non-aqueous (see Palepu et al., Column 3, lines 19-21).

According to the February 2017 FDA Label, supra, before administration to a patient, BENDEKA solution is transferred to an infusion bag containing an aqueous diluent (0.9% sodium chloride, 1.5% dextrose/0.45% sodium chloride, or 5% dextrose), and the resulting solution must be administered within six hours (if the diluent in the infusion bag is sodium chloride or dextrose/sodium chloride aqueous solution) or within three hours (if the diluent in the infusion bag is dextrose aqueous solution), given room temperature and room light storage conditions, to avoid compromising drug stability.

Bendamustine undergoes degradation by hydrolysis. Two hydrolysis products of bendamustine are the monohydroxy and dihydroxy derivatives (4-{5-[(2-chloroethyl)-(2-hydroxyethyl) amino]-1-methyl-1Hbenzimidazol-2yl} butanoic acid (referred to as "HP1") and 4-{5-[bis-(2-hydroxyethyl)amino]-1-methyl-1Hbenzimidazol-2-yl}butanoic acid (referred to as "HP2") (Kasa et al., supra). U.S. Pat. No. 8,791,270 to Brittain and Franklin, relating to lyophilized formulations of bendamustine, notes that "due to its degradation in aqueous solutions (like other nitrogen mustards), bendamustine is supplied as a lyophilized product."

Palepu et al., supra, also refers to the degradation of bendamustine by hydrolysis, including HP1 and HP2, and states "the stability of bendamustine in water is measured in hours, and is therefore, not suitable for long-term storage in liquid form." Additionally, existing commercial liquid formulations of bendamustine, namely BENDEKA™, can freeze even at normal recommended refrigeration temperatures. Thus, the package insert for BENDEKA™ states: "Store BENDEKA at recommended refrigerated storage conditions (2-8° C. or 36-46° F.). When refrigerated, the contents may partially freeze. Allow the vial to reach room temperature (15-30° C. or 59-86° F.) prior to use." TREANDA® Injection, like BENDEKA™, must be stored refrigerated between 2-8° C. TREANDA® Injection requires dilution prior to administration. However, because TREANDA® Injection contains N, N-dimethylacetamide (DMA), the product is incompatible with devices (such as adapters or syringes) containing polycarbonate or ABS (TREANDA U.S. FDA Label dated October 2016). Dilution of TREANDA® Injection using devices containing polycarbonate or ABS leads to device failure (e.g., leaking, breaking, or operational failure), possible product contamination, and potential serious adverse health consequence to the practitioner, including skin reactions, or to the patient, including but not limited to, the risk of small blood vessel blockage if they receive product contaminated with dissolved ABS or polycarbonate (TREANDA U.S. FDA Label dated October 2016).

Thus, there remains a need for a liquid formulation of bendamustine, for therapeutic use in patients, that requires minimal handling during preparation for administration so as to avoid toxic exposure, but remains stable and potent, i.e. with low bendamustine degradation, when stored for significant periods of time.

SUMMARY

This invention provides a concentrated liquid pharmaceutical composition comprising a) a pharmaceutically effective amount of bendamustine or a pharmaceutically acceptable salt thereof, b) a non-aqueous solvent, and c) at least about 2% water v/v of the composition, wherein the pharmaceutical composition is, after dilution, suitable for administration to a mammal by injection.

This invention also provides a concentrated liquid pharmaceutical composition comprising a) a pharmaceutically effective amount of bendamustine or a pharmaceutically acceptable salt thereof, b) a non-aqueous solvent, and c) from about 2% to about 30% water v/v of the composition, wherein the pharmaceutical composition is, after dilution, suitable for administration to a mammal by injection. In other embodiments, the concentrated liquid pharmaceutical composition of the invention comprises a) a pharmaceutically effective amount of bendamustine or a pharmaceutically acceptable salt thereof; b) a non-aqueous solvent; and c) from about 2% to about 25% water v/v of the composition, from about 2% to about 20% water v/v of the composition, from about 2% to about 15% water v/v of the composition, about 2% to about 10% water v/v of the composition, or from about 2% to about 5% water v/v of the composition; and the pharmaceutical composition is, after dilution, suitable for administration to a mammal by injection. In one aspect, the non-aqueous solvent comprises the remaining volume of such composition, such that the composition comprises from about 70% to about 98% v/v non-aqueous solvent when the water comprises from about 2% to about 30% v/v of the composition, from about 75% to about 98% v/v non-aqueous solvent when the water comprises from about 2% to about 25% v/v of the composition, from about 80% to about 98% v/v non-aqueous solvent when the water comprises from about 2% to about 20% v/v of the composition, from about 85% to about 98% v/v non-aqueous solvent when the water comprises from about 2% to about 15% v/v of the composition, from about 90% to about 98% v/v non-aqueous solvent when the water comprises from about 2% to about 10% v/v of the composition, and from about 95% to about 98% v/v non-aqueous solvent when the water comprises from about 2% to about 5% v/v of the composition.

In different embodiments of the concentrated liquid pharmaceutical compositions of the invention described herein, the minimum amount of water in the composition, v/v, can be, in further aspects, from about 2.4%, about 2.8, about 3%, about 3.5%, about 4%, about 5% or about 6%. Accordingly, this invention also provides such concentrated liquid pharmaceutical compositions as described herein which comprise bendamustine or a pharmaceutically acceptable salt thereof, a non-aqueous solvent, and water, wherein:

the amount of water in the composition is from about 2% to about 30% v/v and the amount of non-aqueous solvent is from about 70% to about 98% v/v, the amount of water in the composition is from about 2% to about 25% v/v and the amount of non-aqueous solvent is from about 75% to about 98% v/v, the amount of water in the composition is from about 2% to about 20% v/v and the amount of non-aqueous solvent is from about 80% to about 98% v/v, the amount of water in the composition is from about 2% to about 15% v/v and the amount of non-aqueous solvent is from about 85% to about 98% v/v, the amount of water in the composition is from about 2% to about 10% v/v and the amount of non-aqueous solvent is from about 90% to about 98% v/v, the amount of water in the composition is from about 2% to about 5% v/v and the amount of non-aqueous solvent is from about 95% to about 98% v/v, the amount of water in the composition is from about 2.4% to about 30% v/v and the amount of non-aqueous solvent is from about 70% to about 97.6% v/v, the amount of water in the composition is from about 2.4% to about 25% v/v and the amount of non-aqueous solvent is from about 75% to about 97.6% v/v, the amount of water in the composition is from about 2.4% to about 20% v/v and the amount of non-aqueous solvent is from about 80% to about 97.6% v/v, the amount of water in the composition is from about 2.4% to about 15% v/v and the amount of non-aqueous solvent is from about 85% to about 97.6% v/v, the amount of water in the composition is from about 2.4% to about 10% v/v and the amount of non-aqueous solvent is from about 90% to about 97.6% v/v, the amount of water in the composition is from about 2.4% to about 5% v/v and the amount of non-aqueous solvent is from about 95% to about 97.6% v/v, the amount of water in the composition is from about 2.8% to about 30% v/v and the amount of non-aqueous solvent is from about 70% to about 97.2% v/v, the amount of water in the composition is from about 2.8% to about 25% v/v and the amount of non-aqueous solvent is from about 75% to about 97.2% v/v, the amount of water in the composition is from about 2.8% to about 20% v/v and the amount of non-aqueous solvent is from about 80% to about 97.2% v/v, the amount of water in the composition is from about 2.8% to about 15% v/v and the amount of non-aqueous solvent is from about 85% to about 97.2% v/v, the amount of water in the composition is from about 2.8% to about 10% v/v and the amount of non-aqueous solvent is from about 90% to about 97.2% v/v, the amount of water in the composition is from about 2.8% to about 5% v/v and the amount of non-aqueous solvent is from about 95% to about 97.2% v/v the amount of water in the composition is from about 3% to about 30% v/v and the amount of non-aqueous solvent is from about 70% to about 97% v/v, the amount of water in the composition is from about 3% to about 25% v/v and the amount of non-aqueous solvent is from about 75% to about 97% v/v, the amount of water in the composition is from about 3% to about 20% v/v and the amount of non-aqueous solvent is from about 80% to about 97% v/v, the amount of water in the composition is from about 3% to about 15% v/v and the amount of non-aqueous solvent is from about 85% to about 97% v/v, the amount of water in the composition is from about 3% to about 10% v/v and the amount of non-aqueous solvent is from about 90% to about 97% v/v, the amount of water in the composition is from about 3% to about 5% v/v and the amount of non-aqueous solvent is from about 95% to about 97% v/v, the amount of water in the composition is from about 3.5% to about 30% v/v and the amount of non-aqueous solvent is from about 70% to about 96.5% v/v, the amount of water in the composition is from about 3.5% to about 25% v/v and the amount of non-aqueous solvent is from about 75% to about 96.5% v/v, the amount of water in the composition is from about 3.5% to about 20% v/v and the amount of non-aqueous solvent is from about 80% to about 96.5% v/v, the amount of water in the composition is from about 3.5% to about 15% v/v and the amount of non-aqueous solvent is from about 85% to about 96.5% v/v, the amount of water in the composition is from about 3.5% to about 10% v/v and the amount of non-aqueous solvent is from about 90% to about 96.5% v/v, the amount of water in the composition is from about 3.5% to about 5% v/v and the amount of non-aqueous solvent is from about 95% to about 96.5% v/v, the amount of water in the composition is from about 4% to about 30% v/v and the amount of non-aqueous solvent is from about 70% to about 96% v/v, the amount of water in the composition is from about 4% to about 25% v/v and the amount of non-aqueous solvent is from about 75% to about 96% v/v, the amount of water in the composition is from about 4% to about 20% v/v and the amount of non-aqueous solvent is from about 80% to about 96% v/v, the amount of water in the composition is from about 4% to about 15% v/v and the amount of non-aqueous solvent is from about 85% to about 96% v/v, the amount of water in the composition is from about 4% to about 10% v/v and the amount of non-aqueous solvent is from about 90% to about 96% v/v, the amount of water in the composition is from about 4% to about 5% v/v and the amount of non-aqueous solvent is from about 95% to about 96% v/v, the amount of water in the composition is from about 5% to about 30% v/v and the amount of non-aqueous solvent is from about 70% to about 95% v/v, the amount of water in the composition is from about 5% to about 25% v/v and the amount of non-aqueous solvent is from about 75% to about 95% v/v, the amount of water in the composition is from about 5% to about 20% v/v and the amount of non-aqueous solvent is from about 80% to about 95% v/v, the amount of water in the composition is from about 5% to about 15% v/v and the amount of non-aqueous solvent is from about 85% to about 95% v/v, the amount of water in the composition is from about 5% to about 10% v/v and the amount of non-aqueous solvent is from about 90% to about 95% v/v, the amount of water in the composition is from about 6% to about 30% v/v and the amount of non-aqueous solvent is from about 70% to about 94% v/v, the amount of water in the composition is from about 6% to about 25% v/v and the amount of non-aqueous solvent is from about 75% to about 94% v/v, the amount of water in the composition is from about 6% to about 20% v/v and the amount of non-aqueous solvent is from about 80% to about 94% v/v, the amount of water in the composition is from about 6% to about 15% v/v and the amount of non-aqueous solvent is from about 85% to about 94% v/v, the amount of water in the composition is from about 6% to about 10% v/v and the amount of non-aqueous solvent is from about 90% to about 94% v/v, the amount of water in the composition is from about 5% to about 6% v/v and the amount of non-aqueous solvent is from about 94% to about 95% v/v, the amount of water in the composition is from about 2% to about 4% v/v and the amount of non-aqueous solvent is from about 96% to about 98% v/v, the amount of water in the composition is from about 2.4% to about 4% v/v and the amount of non-aqueous solvent is from about 96% to about 97.6% v/v, the amount of water in the composition is from about 2.8% to about 4% v/v and the amount of non-aqueous solvent is from about 96% to about 97.2% v/v, the amount of water in the composition is from about 3% to about 4% v/v and the amount of non-aqueous solvent is from about 96% to about 97% v/v, the amount of water in the composition is from about 2% to about 3.5% v/v and the amount of non-aqueous solvent is from about 96.5% to about 98% v/v, the amount of water in the composition is from about 2.4% to about 3.5% v/v and the amount of non-aqueous solvent is from about 96.5% to about 97.6% v/v, the amount of water in the composition is from about 2.8% to about 3.5% v/v and the amount of non-aqueous solvent is from about 96.5% to about 97.2% v/v, or the amount of water in the composition is from about 3% to about 3.5% v/v and the amount of non-aqueous solvent is from about 96.5% to about 97% v/v.

In one embodiment, the non-aqueous solvent comprises one or more organic compounds selected from organic polymeric compound solvents and organic small molecule solvents. In another embodiment the non-aqueous solvent comprises one or more organic compounds selected from organic polymeric compound solvents comprising hydroxy moieties and organic small molecule solvents.

In another embodiment, the non-aqueous solvent of the concentrated liquid pharmaceutical composition comprises one or more organic compounds selected from polysorbates, polyethylene glycols, polyalkoxylated castor oils, N,N-dimethylacetamide, dimethyl sulfoxide, 1-methyl-2-pyrrolidinone, and organic small molecule alcohols. In further embodiments, the organic small molecule alcohols are selected from ethanol, isopropyl alcohol, benzyl alcohol, and propylene glycol.

In another embodiment, the non-aqueous solvent of the concentrated liquid pharmaceutical composition according to the invention comprises at least one organic polymeric compound solvent and at least one organic small molecule solvent. Such compositions of the invention comprising a non-aqueous solvent comprising at least one organic polymeric solvent and at least one organic small molecule solvent can comprise, in different aspects: from about 2% water to about 30% water v/v and from about 70% to about 98% v/v non-aqueous organic compound solvents; from about 2% water to about 25% water v/v and from about 75% to about 98% v/v non-aqueous organic compound solvents; from about 2% water to about 20% water v/v and from about 80% to about 98% v/v non-aqueous organic compound solvents; from about 2% water to about 15% water v/v and from about 85% to about 98% v/v non-aqueous organic compound solvents; from about 2% water to about 10% water v/v and from about 90% to about 98% v/v non-aqueous organic compound solvents; or from about 2% water to about 5% water v/v and from about 95% to about 98% v/v non-aqueous organic compound solvents. As described above, in such embodiments as described in this paragraph, the minimum amount of water in the composition can alternatively be from about 2.4%, from about 2.8, from about 3%, from about 3.5%, from about 4%, from about 5% v/v or from about 6% v/v (the total amount of non-aqueous organic compound solvents respectively being a maximum of about 97.6% v/v, 97.2 v/v, 97% v/v, 96.5% v/v, 96% v/v, 95% v/v, or 94% v/v).

In another embodiment, the non-aqueous solvent in a concentrated liquid pharmaceutical composition according to the present invention comprises a polyethylene glycol or a mixture of polyethylene glycols and at least one organic small molecule solvent. In a further embodiment of the invention, the organic small molecule solvent in such a composition is selected from N,N-dimethylacetamide, dimethyl sulfoxide, 1-methyl-2-pyrrolidinone, ethanol, isopropyl alcohol, benzyl alcohol, and propylene glycol. In a further embodiment of the invention, the non-aqueous solvent of the concentrated liquid pharmaceutical composition comprises a polyethylene glycol and ethanol. In another embodiment, the total amount of organic compound solvents (comprising the polyethylene glycol(s) and the organic small molecule solvent) is from about 70% to about 98% v/v.

This invention also provides a concentrated liquid bendamustine pharmaceutical composition as described herein, wherein the composition remains in a liquid state at about 2° C.

As used herein, a "concentrated" pharmaceutical composition is one that has not been reconstituted with water or diluted with water from a prior bendamustine pharmaceutical formulation. A prior bendamustine pharmaceutical formulation means, for example, a lyophilized bendamustine formulation, to which a pharmaceutically acceptable diluent, such as water, must be added to reconstitute the formulation before it is administered by injection to a patient. A prior bendamustine pharmaceutical formulation may also be a liquid concentrated bendamustine pharmaceutical formulation, such as a non-aqueous liquid bendamustine pharmaceutical formulation, to which a diluent, for example a diluent containing water, is added before it is administered by injection to a patient.

In another embodiment, this invention further provides a concentrated liquid pharmaceutical composition as described herein, wherein the non-aqueous solvent comprises at least two different organic compound solvents, and wherein (i) one of the organic compound solvents is a polyethylene glycol or a mixture of polyethylene glycols, (ii) at least one of the organic compound solvents is an organic small molecule solvent, and (iii) the total amount of the non-aqueous organic compounds solvents in the composition is from about 70% to about 98% v/v, from about 75% to about 98% v/v, from about 80% to about 98% v/v, from about 85% to about 98% v/v, from about 90% to about 98% v/v, or from about 95% to about 98% v/v. In different embodiments, the total amount of the water in the composition is from about 2% to about 30% v/v of the composition, when the non-aqueous solvents are from about 70% to about 98% v/v of the composition; from about 2% to about 25% v/v of the composition, when the non-aqueous solvents are from about 75% to about 98% v/v of the composition; from about 2% to about 20% v/v of the composition, when the non-aqueous solvents are from about 80% to about 98% v/v of the composition; from about 2% to about 15% v/v of the composition, when the non-aqueous solvents are from about 85% to about 98% v/v of the composition; from about 2% to about 10% v/v of the composition, when the non-aqueous solvents are from about 90% to about 98% v/v of the composition; or from about 2% to about 5% v/v of the composition, when the non-aqueous solvents are from about 95% to about 98% v/v of the composition. In these embodiments, in one aspect, the amount of polyethylene glycol or mixture of polyethylene glycols in the composition is present in an amount of from about 60% to about 96% v/v (polyethylene glycol(s)/composition). In a further aspect, the amount of polyethylene glycol or mixture of polyethylene glycols in the composition is present in an amount of from about 60% to about 96% v/v in the composition, and the one or more organic small molecule solvents are present in an amount of from about 2% to about 10% v/v in the composition, with the total amount of organic compound solvents in the composition being from about 60% v/v to a maximum of about 98% v/v of the composition. As described above, in such embodiments, the minimum amount of water in the composition can alternatively be from about 2.4%, from about 2.8%, from about 3%, from about 3.5%, from about 4% from about 5% v/v or from about 6% v/v (the total amount of non-aqueous organic compound solvents respectively being a maximum of about 97.6% v/v, 97.2% v/v, 97% v/v, 96.5% v/v, 96% v/v, 95% v/v, or 94% v/v).

The invention also provides a concentrated liquid pharmaceutical composition as described herein, wherein the non-aqueous solvent comprises one or more organic polymeric compound solvents and one or more organic small molecule solvents, and wherein (i) the organic polymeric compound solvents are present in a total amount of from about 60% to about 96% v/v in the composition, (ii) the organic small molecule solvents are present in a total amount of from about 2% to about 10% v/v in the composition, and (iii) the total amount of organic compound solvents in the composition is from about 70% v/v to about 98% v/v of the composition. In one embodiment of such composition, the composition comprises from about 2% to about 30% v/v water and a total of about 70% to about 98% v/v organic compound solvents. In other embodiments of the invention, such concentrated liquid pharmaceutical compositions comprise from about 2% to about 25% v/v water and a total of about 75% to about 98% v/v organic compound solvents; from about 2% to about 20% v/v water and a total of about 80% to about 98% v/v organic compound solvents; from about 2% to about 15% v/v water and a total of about 85% to about 98% v/v organic compound solvents; from about 2% to about 10% v/v water and a total of about 90% to about 98% v/v organic compound solvents; or from about 2% to about 5% v/v water and a total of about 95% to about 98% v/v organic compound solvents. As described hereinabove, in further aspects, in each of the aforementioned embodiments, the minimum amount of water in the composition, v/v, can be from about 2.4%, from about 2.8%, from about 3%, from about 3.5%, from about 4%, from about 5%, or from about 6% (the maximum amount of total organic compound solvents being, respectively about 97.6%, about 97.2, about 97%, about 96.5%, about 96%, about 95%, or about 94% v/v).

Accordingly, this invention provides a concentrated liquid pharmaceutical composition comprising a pharmaceutically effective amount of bendamustine or a pharmaceutically acceptable salt thereof; a non-aqueous solvent comprising one or more organic polymeric compound solvents and one or more organic small molecule solvents, wherein (i) the organic polymeric compound solvents are present in a total amount of from about 60% to about 96% v/v in the composition, (ii) the organic small molecule solvents are present in a total amount of from about 2% to about 10% v/v in the composition, and (iii) the total amount of organic compound solvents in the composition is from about 70% v/v to about 98% v/v of the composition; and at least about 2% water v/v of the composition; wherein the composition is, after dilution, suitable for administration to a mammal by injection. In further embodiments, such a composition comprises at least about 2.4% water v/v, at least about 2.8% water v/v, at least about 3% water v/v, or at least about 3.5% water v/v. In further aspects, such composition comprises from about 2.4% to about 4% v/v water and a total of about 96% to about 97.6% v/v organic compound solvents (the organic compounds solvents comprising the organic polymeric compound solvent(s) and the organic small molecule solvent(s)). In other aspects, such composition comprises from about 3% to about 3.5% v/v water and a total of about 96.5% to about 97% v/v organic compound solvents (the organic compounds solvents comprising the organic polymeric compound solvent(s) and the organic small molecule solvent(s)).

In one aspect of the invention, the concentrated liquid pharmaceutical composition as described herein is ready-to-dilute with a diluent suitable for injection before administration.

The invention also provides a concentrated liquid pharmaceutical composition comprising a) a pharmaceutically effective amount of bendamustine or a pharmaceutically acceptable salt thereof, b) a non-aqueous solvent, and c) water in an amount of from about 2% to about 10%, about 2.1% to about 10%, about 2.2% to about 10%, about 2.3% to about 10%, about 2.4% to about 10%, about 2.5% to about 10%, about 2% to about 4%, about 2.1% to about 4%, about 2.2% to about 4%, about 2.3% to about 4%, about 2.4% to about 4%, about 2.5% to about 4%, about 2.8% to about 4%, about 2.8% to about 3.5%, or about 3% to about 3.5% v/v of the composition, wherein the pharmaceutical composition is, after dilution, suitable for administration to a mammal by injection. In different embodiments, this invention also provides such concentrated liquid pharmaceutical compositions wherein:

the amount of water in the composition is from about 2% to about 10% v/v and the amount of non-aqueous solvent is from about 90% to about 98% v/v, the amount of water in the composition is from about 2.1% to about 10% v/v and the amount of non-aqueous solvent is from about 90% to about 97.9% v/v, the amount of water in the composition is from about 2.2% to about 10% v/v and the amount of non-aqueous solvent is from about 90% to about 97.8% v/v, the amount of water in the composition is from about 2.3% to about 10% v/v and the amount of non-aqueous solvent is from about 90% to about 97.7% v/v, the amount of water in the composition is from about 2.4% to about 10% v/v and the amount of non-aqueous solvent is from about 90% to about 97.6% v/v, the amount of water in the composition is from about 2.5% to about 10% v/v and the amount of non-aqueous solvent is from about 90% to about 97.5% v/v, the amount of water in the composition is from about 2% to about 4% v/v and the amount of non-aqueous solvent is from about 96% to about 98% v/v, the amount of water in the composition is from about 2.1% to about 4% v/v and the amount of non-aqueous solvent is from about 96% to about 97.9% v/v, the amount of water in the composition is from about 2.2% to about 4% v/v and the amount of non-aqueous solvent is from about 96% to about 97.8% v/v, the amount of water in the composition is from about 2.3% to about 4% v/v and the amount of non-aqueous solvent is from about 96% to about 97.7% v/v, the amount of water in the composition is from about 2.4% to about 4% v/v and the amount of non-aqueous solvent is from about 96% to about 97.6% v/v, the amount of water in the composition is from about 2.5% to about 4% v/v and the amount of non-aqueous solvent is from about 96% to about 97.5% v/v, the amount of water in the composition is from about 2.8% to about 4% v/v and the amount of non-aqueous solvent is from about 96% to about 97.2% v/v, the amount of water in the composition is from about 2.8% to about 3.5% v/v and the amount of non-aqueous solvent is from about 96.5% to about 97.2% v/v, and the amount of water in the composition is from about 3% to about 3.5% v/v and the amount of non-aqueous solvent is from about 96.5% to about 97% v/v.

In different embodiments, the concentration of the bendamustine or bendamustine salt in a concentrated liquid pharmaceutical composition of the invention is from about 1 mg/mL to about 100 mg/mL, preferably from about 10 mg/mL to about 100 mg/mL, more preferably from about 20 mg/mL to about 60 mg/mL. In embodiments of the concentrated liquid pharmaceutical compositions herein, the bendamustine or salt thereof is bendamustine hydrochloride. In certain embodiments of the invention, the concentrated liquid pharmaceutical compositions comprise from about 35 to about 40 mg/mL bendamustine or bendamustine salt, for example from about 35 to about 40 mg/mL bendamustine hydrochloride. In other embodiments, the concentrated liquid pharmaceutical compositions comprise about 25 mg/mL bendamustine hydrochloride.

The present invention also provides the concentrated liquid pharmaceutical compositions as described herein, which compositions have a pH of from about 3.3 to about 3.7 when such composition is tested in a water solution at about 12.4% v/v. The concentrated liquid pharmaceutical compositions of the invention may comprise a pH adjuster, such as a strong base, if necessary in an amount sufficient to obtain the pH of from about 3.3 to about 3.7.

This invention also provides a concentrated liquid pharmaceutical composition comprising a pharmaceutically effective amount of bendamustine hydrochloride, wherein the pharmaceutical composition is, after dilution, suitable for administration to a mammal by injection, and wherein each mL of the composition contains 25 mg said bendamustine hydrochloride, 23.7 mg absolute ethanol, 30 mg water, and polyethylene glycol quantity sufficient. In one embodiment of such pharmaceutical composition the polyethylene glycol is polyethylene glycol 400. In a further embodiment, said pharmaceutical composition further comprises an antioxidant. In one embodiment, the antioxidant is butylated hydroxyanisole and the amount of butylated hydroxyanisole is about 1 mg/mL of the pharmaceutical composition.

Accordingly, the invention in one embodiment provides a concentrated liquid pharmaceutical composition comprising a pharmaceutically effective amount of bendamustine hydrochloride, wherein the pharmaceutical composition is, after dilution, suitable for administration to a mammal by injection, and wherein each mL of the composition contains 25 mg said bendamustine hydrochloride, 23.7 mg absolute ethanol, 30 mg water, 1 mg butylated hydroxyanisole, and polyethylene glycol 400 quantity sufficient.

This invention also provides a sealed container containing a concentrated liquid pharmaceutical composition as described herein. In different aspects of the invention, a sealed container containing a concentrated liquid pharmaceutical composition as described herein is provided, wherein the pharmaceutical composition comprises bendamustine hydrochloride in an amount such that the sealed container containing the pharmaceutical composition contains from about 5 mg to about 500 mg, from about 10 mg to about 350 mg, or from about 20 mg to about 300 mg bendamustine hydrochloride. In different embodiments, the amount of bendamustine hydrochloride in the concentrated liquid pharmaceutical composition in the sealed container is such that the sealed container contains 25 mg, 100 mg or 200 mg bendamustine hydrochloride.

In another embodiment, the sealed container contains from about 0.5 mL to about 50 mL of a concentrated liquid pharmaceutical composition of the invention. In one embodiment, the sealed container contains from about 0.5 mL to about 50 mL of a concentrated liquid pharmaceutical composition comprising a pharmaceutically effective amount of bendamustine hydrochloride, wherein the pharmaceutical composition is, after dilution, suitable for administration to a mammal by injection, and wherein each mL of the composition contains 25 mg said bendamustine hydrochloride, 23.7 mg absolute ethanol, 30 mg water, 1 mg butylated hydroxyanisole, and polyethylene glycol 400 quantity sufficient. In different embodiments of the invention, the sealed container contains 1 mL, 4 mL, or 8 mL of such pharmaceutical composition.

DETAILED DESCRIPTION

Bendamustine

The concentrated liquid pharmaceutical compositions of the invention described herein comprise bendamustine or a pharmaceutically acceptable bendamustine salt. Thus, concentrated liquid pharmaceutical compositions of the present invention can comprise bendamustine free base or any pharmaceutically acceptable bendamustine salt, for example bendamustine hydrochloride. Amorphous or hydrated forms of bendamustine or bendamustine pharmaceutically acceptable salt, for example anhydrous bendamustine hydrochloride or bendamustine hydrochloride monohydrate, may be used to make the compositions of the present invention. Other examples of pharmaceutically acceptable salts, besides the hydrochloride salt, that may be used in combination with bendamustine include, but are not limited to hydrobromide, citrate, formate, acetate, and tartrate.

The bendamustine or bendamustine salt is present in the concentrated liquid pharmaceutical compositions of the present invention in a pharmaceutically-effective amount. The treatment of a cancer in a patient, such as a human, may be realized over a dosing regimen requiring multiple effective doses of a composition of the present invention containing bendamustine or a bendamustine salt, separated at intervals, over a period of time. A composition of the present invention may for example contain an effective dose of bendamustine or bendamustine salt of from about 1 mg to about 500 mg, from about 10 mg to about 200 mg, from about 20 mg to about 150 mg, from about 20 mg to about 100 mg, or from about 25 mg to about 100 mg. Preferably a composition of the present invention contains an effective amount of bendamustine or bendamustine salt of about 25 mg, about 50 mg, about 100 mg, or about 200 mg. Preferably the bendamustine or bendamustine salt is bendamustine hydrochloride.

In different embodiments, the concentration of the bendamustine or bendamustine salt in a concentrated liquid pharmaceutical composition of the present invention is from about 1 mg/ml to about 100 mg/ml, from about 10 mg/ml to about 100 mg/ml, from about 20 mg/ml to about 60 mg/ml, from about 20 mg/ml to about 50 mg/ml, from about 25 mg/ml to about 60 mg/ml, and from about 25 mg/ml to about 50 mg/ml. Preferably the concentration of the bendamustine or bendamustine salt in a concentrated liquid pharmaceutical composition of the present invention is about 25 mg/ml, about 30 mg/ml, or about 50 mg/ml. A concentrated liquid pharmaceutical composition of the present invention may contain about 5 mg/ml, about 10 mg/ml, about 20 mg/ml, about 25 mg/ml, about 30 mg/ml, about 35 mg/ml, about 40 mg/ml, about 45 mg/ml, about 50 mg/ml, about 55 mg/ml, or about 60 mg/ml bendamustine or bendamustine salt.

The term "v/v" means "volume per volume" and is used herein to express the concentration of a substance in a solution on a volume per volume basis. By way of example, a solution containing 50% v/v non-aqueous solvents means that there are about 50 ml of combined organic compound solvents in every 100 ml of said solution. As another example, if a solution containing 13.1% v/v ethanol, then every 100 ml of said solution contains about 13.1 ml of ethanol. As further examples, one liter of a pharmaceutical composition of the present invention containing 2.5% v/v water contains 25 ml water, and one liter of a pharmaceutical composition of the present invention containing 3% water contains 30 ml water.

Non-Aqueous Solvent System

The concentrated liquid pharmaceutical compositions of the present invention comprise a non-aqueous solvent system (a "non-aqueous solvent") to assist in the dissolution of the bendamustine or pharmaceutically acceptable bendamustine salt. A non-aqueous solvent system is a single organic compound solvent or combination of organic compound solvents. The non-aqueous solvent system may comprise one or more organic compounds selected from organic polymeric compound solvents and organic small molecule solvents. Organic compound solvents (solvents that are organic compounds) are well known in the art, for example numerous organic alcohols, including organic alcohols of low molecular weight (organic small molecule alcohols) and organic compounds of higher molecular weight containing hydroxy moieties (organic polymeric compounds with hydroxy moieties). In one embodiment, the non-aqueous solvent system comprises an organic polymeric compound solvent, examples including polysorbates (such as polysorbate 80 or polysorbate 20), polyethylene glycols (such as polyethylene glycol 400 or polyethylene glycol 300), and polyalkoxylated castor oils for example a polyethoxylated castor oil (such as CREMOPHOR). In another embodiment, the non-aqueous solvent system comprises an organic small molecule solvent, such as N,N-dimethylacetamide (DMA), dimethyl sulfoxide, 1-methyl-2-pyrrolidinone, or an organic small molecule alcohol (for example ethanol, isopropyl alcohol, benzyl alcohol, or propylene glycol). An organic small molecule solvent generally has a molecular weight of less than about 200 atomic mass units, whereas a polymeric compound generally has an average molecular weight of at least about 300 atomic mass units.

The non-aqueous solvent system in the concentrated liquid pharmaceutical composition of the present invention can comprise one, two, three, four, five, six, seven, eight, nine, ten or more different organic compound solvents.

In different embodiments, the total amount of the organic compound solvents in a concentrated liquid pharmaceutical composition of the present invention is any amount within from about 70% to about 98% v/v of the composition. In other embodiments, the total amount of the organic compound solvents in a composition of the present invention is from about 75% to about 98% v/v, from about 80% to about 98% v/v, from about 85% to about 98% v/v, from about 90% to about 98% v/v, or from about 95% to about 98% v/v. In other embodiments, the total amount of the organic compound solvents in a composition of the present invention is from about 70% to about 96.6% v/v, from about 75% to about 97.6% v/v, from about 80% to about 97.6% v/v, from about 85% to about 97.6% v/v, from about 90% to about 97.6% v/v, or from about 95% to about 97.6% v/v. In other embodiments, the total amount of the organic compound solvents in a composition of the present invention is from about 70% to about 97% v/v, from about 75% to about 97% v/v, from about 80% to about 97% v/v, from about 85% to about 97% v/v, from about 90% to about 97% v/v, or from about 95% to about 97% v/v. In other embodiments, the total amount of the organic compound solvents in a composition of the present invention is from about 70% to about 96.5% v/v, from about 75% to about 96.5% v/v, from about 80% to about 96.5% v/v, from about 85% to about 96.5% v/v, from about 90% to about 96.5% v/v, or from about 95% to about 96.5% v/v. In other embodiments, the total amount of the organic compound solvents in a composition of the present invention is from about 70% to about 96% v/v, from about 75% to about 96% v/v, from about 80% to about 96% v/v, from about 85% to about 96% v/v, from about 90% to about 96% v/v, or from about 95% to about 96% v/v. In other embodiments, the total amount of the organic compound solvents in a concentrated liquid pharmaceutical composition of the present invention is from about 70% to about 95% v/v, from about 75% to about 95% v/v, from about 80% to about 95% v/v, from about 85% to about 95% v/v, or from about 90% to about 95% v/v. In other embodiments, the total amount of the organic compound solvents in a concentrated liquid pharmaceutical composition of the present invention is from about 70% to about 94% v/v, from about 80% to about 94% v/v, from about 85% to about 94% v/v, or from about 90% to about 94% v/v.

Preferably, a concentrated liquid pharmaceutical composition of the present invention comprises one organic polymeric compound solvent and one organic small molecule solvent, and the amount of the organic polymeric compound solvent in the composition is greater (on a v/v basis) than the amount of the organic small molecule solvent. Without being bound by theory, the inventors understand that the organic polymeric compounds are generally less reactive with the bendamustine in the composition than are any single organic small molecule solvent in the composition, and have thus found it possible to include a greater amount of an organic polymeric compound solvent in the composition than an organic small molecule solvent without compromising the long-term stability of the bendamustine or bendamustine salt in the composition. On the other hand, the inclusion of an organic small molecule solvent aids in reducing the viscosity of the composition, thereby rendering a composition that is more suitable for injection.

In one embodiment, the non-aqueous solvent system in a concentrated liquid pharmaceutical composition of the invention comprises one or more organic polymeric compound solvents in a total amount of from about 68% to about 96% v/v in the composition and one or more organic small molecule solvents in a total amount of from about 2% to about 10% v/v in the composition, with a total amount of organic compound solvents in the composition being a maximum of about 98% v/v of the composition. In one embodiment, the non-aqueous solvent system in a concentrated liquid pharmaceutical composition of the present invention contains a polyethylene glycol and an organic small molecule solvent. In another embodiment, the non-aqueous solvent system in a concentrated liquid pharmaceutical composition of the present invention contains a polyethylene glycol and ethanol. In one embodiment, the non-aqueous solvent system in a concentrated liquid pharmaceutical composition of the present invention contains polyethylene glycol 400 and ethanol. In another embodiment, the non-aqueous solvent system in a concentrated liquid pharmaceutical composition of the present invention contains polyethylene glycol 300 and ethanol. In another embodiment, the non-aqueous solvent system in a concentrated liquid pharmaceutical composition of the present invention contains a mixture of polyethylene glycol 300 and polyethylene glycol 400 and ethanol.

Additional Components

The concentrated liquid pharmaceutical compositions of the present invention additionally comprise at least about 2% v/v water. In different embodiments, a concentrated liquid pharmaceutical composition of the present invention comprises at least about 2.1%, at least about 2.2%, at least about 2.3%, at least about 2.4%, at least about 2.5%, at least about 2.8%, at least about 3% v/v water, at least about 3.5% v/v water, at least about 4% v/v water, at least about 5% v/v water, or at least about 6% v/v water. Preferably, a concentrated liquid pharmaceutical composition of the present invention comprises from at least about 2% v/v water to about 30% v/v water, to about 25% v/v water, to about 20% v/v water, to about 15% v/v water, to about 10% v/v water, or to about 5% v/v water (i.e. from about 2% v/v water to about 5% v/v water). In different embodiments, a concentrated liquid pharmaceutical composition of the present invention comprises from about 2% to about 30%, about 2.1% to about 30%, about 2.2% to about 30%, about 2.3% to about 30%, about 2.4% to about 30%, about 2.5% to about 30%, about 2.8% to about 30%, about 3% to about 30%, about 3.5% to about 30%, about 4% to about 30%, about 5% to about 30% v/v water, or about 6% to about 30% v/v water.

In other embodiments, a concentrated liquid pharmaceutical composition of the present invention comprises from about 2% to about 25%, about 2.1% to about 25%, about 2.2% to about 25%, about 2.3% to about 25%, about 2.4% to about 25%, about 2.5% to about 25%, about 2.8% to about 25%, about 3% to about 25%, about 3.5% to about 25%, about 4% to about 25%, about 5% to about 25%, or about 6% to about 25% v/v water.

In other embodiments, a concentrated liquid pharmaceutical composition of the present invention comprises from about 2% to about 20%, about 2.1% to about 20%, about 2.2% to about 20%, about 2.3% to about 20%, about 2.4% to about 20%, about 2.5% to about 20%, about 2.8% to about 20%, about 3% to about 20%, about 3.5% to about 20%, about 4% to about 20%, about 5% to about 20%, or about 6% to about 20% v/v water.

In other embodiments, a concentrated liquid pharmaceutical composition of the present invention comprises from about 2% to about 15%, about 2.1% to about 15%, about 2.2% to about 15%, about 2.3% to about 15%, about 2.4% to about 15%, about 2.5% to about 15%, about 2.8% to about 15%, about 3% to about 15%, about 3.5% to about 15%, about 4% to about 15%, about 5% to about 15%, or about 6% to about 15% v/v water.

In other embodiments, a concentrated liquid pharmaceutical composition of the present invention comprises from about 2% to about 10%, about 2.1% to about 10%, about 2.2% to about 10%, about 2.3% to about 10%, about 2.4% to about 10%, about 2.5% to about 10%, about 2.8% to about 10%, about 3% to about 10%, about 3.5% to about 10%, about 4% to about 10%, about 5% to about 10%, or about 6% to about 10% v/v water.

In other embodiments, a concentrated liquid pharmaceutical composition of the present invention comprises from about 2% to about 5%, about 2.1% to about 5%, about 2.2% to about 5%, about 2.3% to about 5%, about 2.4% to about 5%, about 2.5% to about 5%, about 2.8% to about 5%, about 3% to about 5%, about 3.5% to about 5%, or about 4% to about 5% v/v water.

In other embodiments, a concentrated liquid pharmaceutical composition of the present invention comprises from about 2% to about 4%, about 2.1% to about 4%, about 2.2% to about 4%, about 2.3% to about 4%, about 2.4% to about 4%, about 2.5% to about 4%, about 2.8% to about 4%, about 2.8% to about 3.5%, about 3% to about 4%, about 2% to about 3.5%, about 2.4% to about 3.5%, about 2.8% to about 3.5%, or about 3% to about 3.5% v/v water.

A concentrated liquid pharmaceutical composition of the present invention may optionally contain additional ingredients known in the art to be used in connection with injectable pharmaceutical compositions.

For example, a concentrated liquid pharmaceutical composition of the present invention may optionally contain one or more antioxidants. Antioxidants known in the art may be used in the compositions of the invention, for example sodium bisulfite, sodium sulfite, sodium metabisulfite, ascorbic acid, sodium EDTA, monothioglycerol, L-cysteine, thioglycolic acid, thiosorbitol, butylated hydroxyanisole, butylated hydroxytoluene, glutathione, gentisic acid, lipoic acid, ascorbityl palmitate, propyl gallate, nordihydroguaiaretic acid, or a combination thereof. In one embodiment of the invention, the antioxidant is a chain terminator, i.e. a chemical substance capable of donating a hydrogen radical, thereby possessing the ability to terminate free radical chain reactions occurring in other compounds due to oxidative stress. In one embodiment of the invention, the antioxidant is a sulfhydryl compound, for example an antioxidant comprising an —SH moiety such as monothioglycerol, L-cysteine, thioglycolic acid or thiosorbitol. Preferably, an antioxidant used in a composition of the present invention is a phenol antioxidant, i.e. an antioxidant comprising one or more phenolic hydroxy groups for example butylated hydroxyanisole, butylated hydroxytoluene, propyl gallate or nordihydroguaiaretic acid.

When calculated on a v/v basis, the amounts of bendamustine or bendamustine salt and optional additional ingredients (e.g. pH adjustor or antioxidant) in a concentrated liquid pharmaceutical composition of the present invention are negligible on a v/v basis. Thus, the organic solvents and the water comprise the detectable volume of a composition of the present invention when measured by standard volumetric glassware methods. About 100% of the volume of a concentrated liquid pharmaceutical composition of the present invention is the organic solvents and the water. A small, negligible amount of volume is taken up by the 1) bendamustine or bendamustine salt, and 2) pH adjuster and antioxidant (to the extent either is included in the composition of the invention).

pH

In one embodiment, the pH of a concentrated liquid pharmaceutical composition of the present invention is between about 3.30 to about 3.70, when the pH of such composition is tested in a water solution at about 12.4% v/v. In another embodiment, the pH of a concentrated liquid pharmaceutical composition of the present invention is between about 3.40 to about 3.60, when the pH of such composition is tested in a water solution at about 12.4% v/v. In different embodiments, the pH of a concentrated liquid pharmaceutical composition of the present invention is from about 3.30, about 3.37, or about 3.45 to about 3.70, when the pH of such composition is tested in a water solution at about 12.4% v/v. In different embodiments, the pH of a concentrated liquid pharmaceutical composition of the present invention is from about 3.30, about 3.37, or about 3.45 to about 3.66, when the pH of such composition is tested in a water solution at about 12.4% v/v. In different embodiments, the pH of a concentrated liquid pharmaceutical composition of the present invention is from about 3.30, about 3.37, or about 3.45 to about 3.57, when the pH of such composition is tested in a water solution at about 12.4% v/v.

Methods for adjusting pH of a pharmaceutical composition are well known in the art, and any such method can be used to adjust the pH of a composition of the present invention to achieve a preferred pH as described herein. If necessary, for example, to achieve a preferred pH as described herein, a strong base may be added to a composition of the present invention. Examples of strong bases that can be used in pharmaceutical compositions of the present invention to adjust pH are well known in the art and include, but are not limited to, NaOH and KOH.

For example, the strong base may be increasingly titrated into a formulation until a desired pH is obtained. After adding a small amount of strong base, an aliquot of the concentrated liquid pharmaceutical composition may be taken and combined with water to about 12.4% v/v composition/water. The pH of the resulting solution may be tested with a calibrated pH meter. Thus, the pH of the concentrated liquid pharmaceutical composition may be determined. If necessary, the process is repeated until the desired pH for the concentrated liquid pharmaceutical composition is obtained.

Stable Presentations and Dosage Forms

Compositions of the present invention can be provided in unit presentations. Each unit presentation can contain a single dose or multiple-doses of a composition of the present invention. For example a unit containing a composition of the present invention may contain one, two, three, four, five, six, seven, eight, nine, ten or more doses. The units may be provided in any suitable type of sealed container known to those in the art. For example the units may be packaged and provided in vials, syringes, sealed bottles, or sealed bags made of pharmaceutically acceptable material, such as glass or pharmaceutically acceptable plastic.

In different embodiments, the present invention provides a sealed container containing a concentrated liquid pharmaceutical composition of the present invention containing 25 mg bendamustine HCl, 50 mg bendamustine HCl, 100 mg bendamustine HCl, 150 mg bendamustine HCl, 200 mg bendamustine HCl, 250 mg bendamustine HCl, 300 mg bendamustine HCl, 500 mg bendamustine HCl, or 1000 mg bendamustine HCl.

The sealed units containing the concentrated liquid pharmaceutical compositions of the present invention may be suitable for long term storage, prior to administration. The sealed units containing the concentrated liquid pharmaceutical compositions of the present invention may be suitable for long term storage under standard refrigeration temperatures. A standard refrigeration temperature is from 2° C. to 8° C. For example, sealed units containing the concentrated liquid pharmaceutical compositions of the present invention may be suitable for storage under standard refrigeration conditions for up to about one week, up to about three weeks, up to about 1 month, up to about six weeks, up to about 3 months, up to about 6 months, up to about 12 months, up to about 18 months, up to about 24 months, or up to about 36 months. "Suitable for storage" means that a concentrated liquid pharmaceutical composition of the present invention is stable overtime, it remains liquid, does not significantly degrade and does not significantly lose its potency, over time, under standard refrigeration conditions.

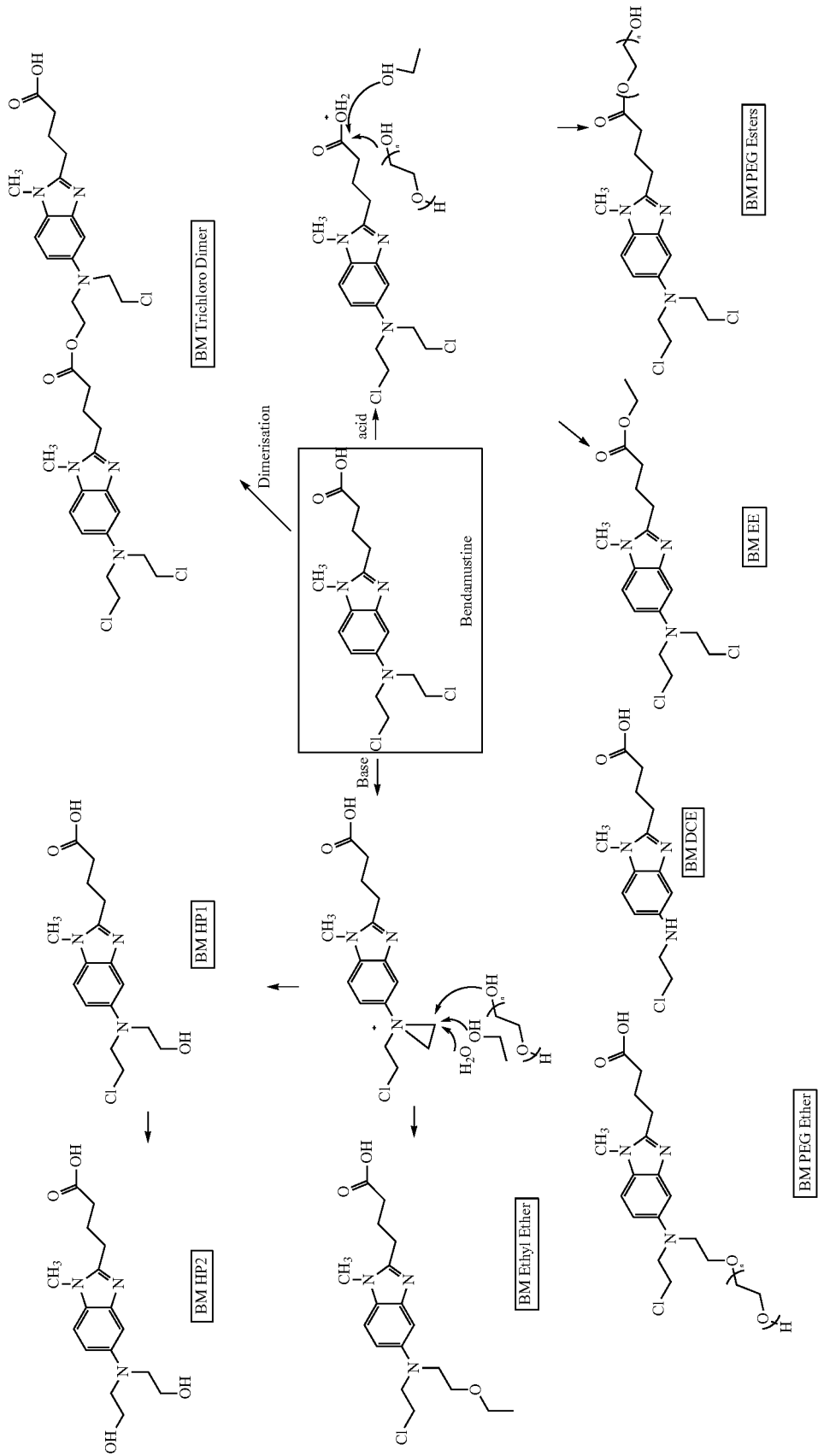

Scheme 1 illustrates different bendamustine degradation reactions that may occur in various environments. Upon reaction with water over time, bendamustine hydrolysis products BM HP1 and BM HP2 may occur, with BM HP1 predominating over BM HP2. As depicted in Scheme 1, increasing pH, i.e. a relatively more basic environment, favors bendamustine hydrolysis degradation. Bendamustine reaction with alcohols at relatively higher pH's (the "Base" direction in Scheme 1) is believed to result in bendamustine alkyl ether degradants. For example, reaction at a higher pH with ethanol and polyethylene glycol can result in, respectively, bendamustine ethyl ether ("BM Ethyl Ether") and bendamustine polyethylene glycol ethers ("BM PEG Ether"). As pH decreases (the "Acid" direction in Scheme 1), dimerisation may occur, resulting in bendamustine trichloro dimer over time ("BM Trichloro Dimer"). Additionally, at lower pH ("Acid" direction in Scheme 1), reaction with alcohols forms bendamustine alkyl ester degradants, for example bendamustine ethyl ester ("BM EE") from bendamustine reaction with ethanol and bendamustine polyethylene glycol esters ("BM PEG Esters") from bendamustine reaction with polyethylene glycol. An additional bendamustine degradant is bendamustine de-chloroethyl ("BM DOE"), which the present inventors hypothesize (without being bound by such theory) is formed by a radical mechanism. Such bendamustine degradants are alternatively referred to herein as "bendamustine related substances", "related substances" or "impurities".

The sealed containers and concentrated liquid pharmaceutical compositions therein may be sterilized by methods known in the art, for example by aseptic filtration, terminal sterilization (autoclaving or irradiation), or any combination thereof, thus obtaining sealed containers of sterile concentrated liquid pharmaceutical compositions of the present invention.

Methods of Treatment

The present invention provides a method of treating a cancer in a mammal, comprising administering an effective amount of a concentrated liquid pharmaceutical composition as described herein to the mammal. In different embodiments of the method of treating cancer in a mammal of the present invention, the cancer is a leukemia or a lymphoma. In other aspects of the invented method for treating cancer in a mammal, the cancer is chronic lymphocytic leukemia or non-Hodgkin lymphoma.

The therapeutic methods of the invention comprise diluting an effective amount of a concentrated liquid pharmaceutical composition of the present invention with a pharmaceutically acceptable diluent, and administering the resulting diluted pharmaceutical composition containing the effective amount of the concentrated liquid pharmaceutical composition to a mammal in need thereof by injection. The effective amount of a concentrated liquid pharmaceutical composition of the present invention for treating cancer, for example chronic lymphocytic leukemia (CLL) or non-Hodgkin Lymphoma (NHL), can be determined by a person of ordinary skill in the art, for example by reference to approved methods for treating CLL or NHL using already approved drugs containing bendamustine or a bendamustine salt, such as the drugs BENDEKA™ and TREANDA®. The effective amount can be adjusted by a person of ordinary skill in the art based on the condition and size (body surface area in, for example, square meters) of the patient being treated.

The concentrated liquid pharmaceutical compositions of the present invention are designed for administration, after dilution, to a mammal by injection. The diluted compositions may be administered to a patient by intravenous (IV) infusion. For administration by IV infusion, a pharmaceutically effective volume of concentrated liquid pharmaceutical composition of the invention may be aseptically withdrawn from the container containing the composition and transferred to, or may be injected aseptically into (from the container (e.g. syringe) containing the composition), an infusion bag containing a suitable pharmaceutically acceptable diluent, for example 0.9% sodium chloride, 2.5% dextrose/0.45% sodium chloride, or 5% dextrose. The concentration of bendamustine or bendamustine salt in a diluted formulation just prior to administration to the patient is preferably within a range of about 0.1 mg/mL to about 10 mg/mL. In different embodiments of the present invention, the concentration of bendamustine or bendamustine salt in a diluted formulation just prior to administration to a patient is from about 1 mg/mL or about 1.5 mg/mL to about 7 mg/mL or about 8 mg/mL, for example from about 1.85 mg/mL to about 5.6 mg/mL. In other embodiments of the present invention, the concentration of bendamustine salt in a diluted formulation just prior to administration to a patient is within a range of about 0.1 mg/mL to about 1.85 mg/mL, for example from about 0.2 mg/mL about 0.6 mg/mL or 0.7 mg/mL. As described herein, a concentrated liquid pharmaceutical composition of the present invention may be diluted in a diluent suitable for injection (for example a pharmaceutically acceptable diluent contained in an infusion bag) just prior to administration to a mammal in need thereof to achieve such bendamustine (or bendamustine salt) concentration of from about 0.1 mg/mL to about 10 mg/mL.

Methods of Preparation

The present invention also provides methods of preparing concentrated liquid pharmaceutical compositions as described herein. In one embodiment, the invention provides a method for preparing a concentrated liquid pharmaceutical composition, which method comprises combining: a) bendamustine or a pharmaceutically acceptable salt thereof, b) one or more organic compounds selected from organic polymeric compound solvents and organic small molecule solvents, c) at least about 2% water v/v (water/pharmaceutical composition), and d) optionally, one or more antioxidants. Preferably, ingredient (c) is from about 2% to a maximum of about 10% water v/v (water/pharmaceutical composition). In a further embodiment of this method, after combining the ingredients (a)-(c), and optionally (d): i) the pH of an aqueous solution containing about 12.4% volume of said concentrated liquid pharmaceutical composition is measured; ii) if the pH of (i) is not from about 3.4 to about 3.6, a pH adjuster is added to the concentrated liquid pharmaceutical composition; and iii) steps (i) and (ii) are repeated, if necessary, until the pH of an aqueous solution containing about 12.4% of the concentrated liquid pharmaceutical composition v/v is from about 3.4 to about 3.6.

In another embodiment, the invention provides a method for preparing a concentrated liquid pharmaceutical composition, which method comprises 1) combining a) bendamustine or a pharmaceutically acceptable salt thereof, b) optionally, one or more antioxidants, c) water, d) one or more organic small molecule solvents, and e) one or more organic polymeric compound solvents; 2) agitating the combination resulting from step (1) of the method until the bendamustine or pharmaceutically acceptable salt thereof and the antioxidant or antioxidants, if present, are dissolved; and 3) adding a further amount of the organic polymeric compound solvent or organic polymeric compound solvents sufficient to obtain a concentrated liquid pharmaceutical composition comprising at least about 2% water v/v (water/pharmaceutical composition). Preferably, the water and organic solvents in steps (1) and (2) of the method are combined in amounts sufficient to obtain a concentrated liquid pharmaceutical composition comprising from about 2% to a maximum of about 10% water v/v (water/pharmaceutical composition). In a further aspect of this method, the method further comprises, after step (3), (i) measuring the pH of an aqueous solution containing about 12.4% volume of the concentrated liquid pharmaceutical composition v/v; (ii) if the pH of (i) is not from about 3.4 to about 3.6, adding a pH adjuster to the concentrated liquid pharmaceutical composition; and (iii) repeating steps (i) and (ii), if necessary, until the pH of an aqueous solution containing about 12.4% of the concentrated liquid pharmaceutical composition v/v is from about 3.4 to about 3.6.

The steps of the methods of preparation described herein are carried out under pharmaceutically acceptable conditions for sterility and manufacturing.

The bendamustine or pharmaceutically acceptable bendamustine salt used in the aforementioned methods of preparation of the invention may be a pharmaceutically acceptable amount of bendamustine or pharmaceutically acceptable bendamustine salt. However, concentrated liquid pharmaceutical compositions of the present invention can be prepared in batch quantities, if desired, using the aforementioned methods of the invention.

Preferably, the amount of the organic polymeric compound solvents in the methods of preparation described herein is greater than the amount of the organic small molecule solvents used, when the amounts of such solvents are calculated on a v/v basis relative to the resulting concentrated liquid pharmaceutical composition. The organic small molecule solvents and the organic polymeric compound solvents that can be used in the methods of preparation of the invention are as described herein. Preferably, the organic polymeric compound solvent is a polyethylene glycol, such as PEG 300 or PEG 400. Preferably, the organic compound small molecule solvent is a small molecule alcohol, for example ethanol, propylene glycol, benzyl alcohol or isopropyl alcohol).

Any pH adjuster known in the art can be used in the methods of preparation described herein. The pH adjuster may, for example, be a strong base such as NaOH or KOH. The bendamustine, bendamustine salt, optional antioxidant or antioxidants and optional pH adjuster may be dissolved into the concentrated liquid pharmaceutical compositions in the methods described herein by agitation during the methods, and such techniques (e.g. mixing) are known to those of ordinary skill in the art.

As described hereinabove, the concentrated liquid bendamustine compositions so prepared can be packaged in sterile, sealed containers, such as vials, syringes, bottles or bags, thereby providing pharmaceutically acceptable unit presentations of concentrated liquid pharmaceutical compositions of the present invention suitable for storage and transport.

EXAMPLES

The following examples are provided to illustrate certain aspects of the present invention. These Examples should not be considered as limiting the scope of the invention, as more fully described herein and set forth in the appended claims.

Example 1: Preparation of 25 m/mL Bendamustine HCl Liquid Injection Formulations One mL units of 25 mg/mL bendamustine HCl formulations according to the present invention were made consisting of the materials outlined in the following Table 1:

TABLE 1

Bulk Formulation of Bendamustine Formulation B Type

| Material | Quantity |
| --- | --- |
| Bendamustine HCl | 25 mg/mL |
| Butylated hydroxyanisole | 1 mg/mL |
| Ethanol | See Table 2 |
| Water for Injection (WFI) | See Table 2 |
| PEG 400 | Quantity sufficient to 1 mL |

("PEG 400" is polyethylene glycol 400)

To prepare the above described one mL units, a bulk solution was manufactured as follows, under yellow light as far as practical: 6.25 grams of bendamustine hydrochloride was added to a 250 mL volumetric flask. 250 mg of butylated hydroxyanisole (BHA) was added. Approximately 200 mL of PEG 400 was added to the 250 mL flask. A predetermined amount of absolute ethanol was added to the flask (see the following Table 2). The predetermined volume of Water for Injection (WFI) was then added to the flask (see the following Table 2). The bendamustine HCl and the BHA were then dissolved by swirling or shaking the flask. The solution was then filled to volume with PEG 400 so as to obtain a 25 mg/mL bendamustine HCl solution. The flask was repeatedly inverted until a homogenous solution was achieved. The pH was adjusted using 5N NaOH to a target of 3.5 (range of 3.4 to 3.6). The bulk solution was filtered through a 0.2-micron pore size polyvinylidene fluoride (PVDF) membrane filter.

TABLE 2

25 mg/mL Bendamustine Formulations "B"

| Formulation | WFI (% v/v) | Ethanol (% v/v) | Amount per 250 mL Formulation | |
| --- | --- | --- | --- | --- |
| | | | WFI (mL) | Ethanol (mL) |
| B1 | 0.0 | 5.0 | 0 | 12.5 |
| B2 | 5.0 | 5.0 | 12.5 | 12.5 |
| B3 | 5.0 | 0.0 | 12.5 | 0 |
| B4 | 5.0 | 10.0 | 12.5 | 25 |
| B5 | 5.0 | 5.0 | 12.5 | 12.5 |
| B6 | 10.0 | 5.0 | 25 | 12.5 |
| B7 | 5.0 | 5.0 | 12.5 | 12.5 |
| B8 | 5.0 | 5.0 | 12.5 | 12.5 |
| B9 | 8.5 | 8.5 | 21.25 | 21.25 |
| B10 | 8.5 | 1.5 | 21.25 | 3.75 |
| B11 | 1.5 | 8.5 | 3.75 | 21.25 |
| B12 | 1.5 | 1.5 | 3.75 | 3.75 |
| B13 | 5.0 | 5.0 | 12.5 | 12.5 |

Example 2

PH Assessment of Bendamustine Formulations

A study was conducted to assess the effect of different pH levels on the formulation stability of bendamustine HCl formulations. Bendamustine bulk liquid formulation was prepared using bendamustine HCl, absolute alcohol (ethanol), Water for Injection (WFI), and PEG 400 (polyethylene glycol 400). The bulk formulation contained 25 mg/mL bendamustine HCl, 1 mg/mL butylated hydroxyanisole, 3.0% absolute alcohol and 3% v/v WFI (water for injection), made up to volume with PEG 400. The bulk was then pH-adjusted with 5N NaOH to obtain said formulation having the different pH values set forth in Table 3.

To determine the pH of a 25 mg/mL bendamustine HCl formulation prepared as set forth in this Example, a 0.55±0.05 gram aliquot of a pH-adjusted formulation was prepared. 3.5 mL water was added, and the combination was mixed gently until visually homogenous, thereby obtaining a 12.3% v/v solution of the chosen bendamustine HCl liquid formulation in water. The pH of the solution in the flask was then measured using a calibrated pH meter.

Having thus obtained 25 mg/mL bendamustine HCl formulations with different identified pH, said formulations were then filled into 2 mL vials, at approximately 1.5 mL per vial.

The bendamustine stability was measured over time for the formulations having the various pH. Bendamustine related substances were detected in the formulations over time by HPLC (high performance liquid chromatography).

The HPLC test method used was as follows:

| Method Requirement | Description |
| --- | --- |
| Column | L1(Octyldecylsilane, 250 × 4.6 mm, 5 μm |
| Column temperature | 25° C. |
| Sample temperature | 5° C. |
| Detector wavelength | 260 nm |
| Flow rate | 1.1 mL/minute |
| Injection volume | 15 μL |
| Mobile phase A | 0.06M ammonium formate in WFI (pH 3.2): Acetonitrile (90:10) |
| Mobile Phase B | 0.06M ammonium formate in WFI (pH 3.2): Acetonitrile (30:70) |

|  | Time | A (%) | B (%) |
| --- | --- | --- | --- |
| Gradient | 0 | 100 | 0 |
|  | 3 | 100 | 0 |
|  | 7 | 93 | 7 |
|  | 12 | 80 | 20 |
|  | 33 | 40 | 60 |
|  | 36 | 0 | 100 |
|  | 38 | 100 | 0 |
|  | 55 | 100 | 0 |

| Run time | 55 minutes |
| --- | --- |
| Diluent | Methanol |
| Sample solution concentration | 0.4 mg/mL |

Amounts of related substances in a sample are expressed as a percentage-namely area under the curve (AUC) of the peak located for the related substance in a test sample output relative to the AUC of the bendamustine peak in the bendamustine standard. In the following Tables and description, "ND" means "not detected". "RRT" means "relative retention time". "T" equals "number of months", such that "T0" is the initial starting time, and "T6", for example, is six months later.

The following Table 3 lists the test results from the bendamustine HCl pH stability studies at various points over time for the BM DCE impurity at 25° C.:

TABLE 3

Effect of pH on BM DCE level

| Sample at 25° C. | T0 | T1 | T2 | T4 | T6 |
| --- | --- | --- | --- | --- | --- |
| pH 3.23 | ND | 0.09% | 0.13% | 0.20% | 0.30% |
| pH 3.30 | ND | 0.05% | 0.07% | 0.11% | 0.15% |
| pH 3.37 | ND | 0.06% | 0.09% | 0.14% | 0.20% |
| pH 3.45 | ND | 0.07% | 0.11% | 0.18% | 0.25% |
| pH 3.57 | ND | 0.09% | 0.15% | 0.25% | 0.36% |
| pH 3.66 | ND | 0.11% | 0.19% | 0.32% | 0.49% |
| pH 3.78 | ND | 0.13% | 0.25% | 0.42% | 0.61% |

Table 3 illustrates that with time at pH levels higher than 3.30 at 25° C., the BM DCE impurity levels increase.

The following Table 4 lists the test results from the bendamustine HCl pH studies from T0 to T6 for the BM HP1 impurity at 25° C.:

TABLE 4

Effect of pH on BM HP1 level

| Sample at 25° C. | T0 | T1 | T2 | T4 | T6 |
| --- | --- | --- | --- | --- | --- |
| pH 3.23 | ND | 0.02% | 0.02% | 0.03% | 0.04% |
| pH 3.30 | ND | 0.03% | 0.03% | 0.06% | 0.08% |
| pH 3.37 | ND | 0.04% | 0.05% | 0.10% | 0.14% |
| pH 3.45 | 0.03% | 0.05% | 0.07% | 0.13% | 0.19% |
| pH 3.57 | 0.02% | 0.06% | 0.10% | 0.18% | 0.27% |
| pH 3.66 | 0.03% | 0.08% | 0.13% | 0.24% | 0.36% |
| pH 3.78 | 0.02% | 0.09% | 0.17% | 0.31% | 0.47% |

Table 4 illustrates that with time at higher pH levels at 25° C., the BM HP1 impurity levels increase.

TABLE 5

Effect of pH on BM PEG Ethers level

| Sample at 25° C. | T0 | T1 | T2 | T4 | T6 |
| --- | --- | --- | --- | --- | --- |
| pH 3.23 | ND | ND | ND | 0.02% | 0.05% |
| pH 3.30 | ND | ND | 0.02% | 0.07% | 0.08% |
| pH 3.37 | 0.01% | ND | 0.05% | 0.11% | 0.11% |
| pH 3.45 | 0.02% | 0.02% | 0.08% | 0.13% | 0.14% |
| pH 3.57 | 0.02% | 0.03% | 0.12% | 0.21% | 0.23% |
| pH 3.66 | 0.03% | 0.07% | 0.14% | 0.26% | 0.38% |
| pH 3.78 | 0.04% | 0.08% | 0.19% | 0.35% | 0.48% |

Table 5 illustrates that with time at higher pH levels at 25° C., the BM PEG Ether group of impurities increases.

TABLE 6

Effect of pH on BM PEG Esters level

| Sample at 25° C. | T0 | T1 | T2 | T4 | T6 |
| --- | --- | --- | --- | --- | --- |
| pH 3.23 | ND | 1.64% | 3.36% | 6.54% | 10.92% |
| pH 3.30 | ND | 0.17% | 0.41% | 0.82% | 1.17% |
| pH 3.37 | ND | 0.11% | 0.25% | 0.51% | 0.71% |
| pH 3.45 | ND | 0.09% | 0.22% | 0.40% | 0.61% |
| pH 3.57 | ND | 0.09% | 0.20% | 0.35% | 0.62% |
| pH 3.66 | ND | 0.07% | 0.19% | 0.30% | 0.65% |
| pH 3.78 | ND | 0.04% | 0.18% | 0.30% | 0.96% |

Table 6 illustrates that with time a lower pH levels less than 3.30 at 25° C., the BM PEG Ester group of impurities increases significantly than compared to higher pH levels.

TABLE 7

Effect of pH on BM Trichloro Dimer level

| Sample at 25° C. | T0 | T1 | T2 | T4 | T6 |
| --- | --- | --- | --- | --- | --- |
| pH 3.23 | ND | 0.06% | 0.21% | 0.38% | 0.35% |
| pH 3.30 | ND | 0.02% | 0.03% | 0.06% | 0.08% |
| pH 3.37 | ND | 0.02% | 0.04% | 0.05% | * |
| pH 3.45 | ND | 0.03% | 0.05% | 0.12% | * |
| pH 3.57 | ND | 0.04% | 0.07% | 0.16% | * |

TABLE 7-continued

Effect of pH on BM Trichloro Dimer level

| Sample at 25° C. | T0 | T1 | T2 | T4 | T6 |
|---|---|---|---|---|---|
| pH 3.66 | ND | 0.06% | 0.11% | 0.23% | * |
| pH 3.78 | ND | 0.09% | 0.18% | 0.35% | * |

*Co-elution with BM PEG Esters therefore could not accurately determine their levels.

Table 7 illustrates that with time the BM Trichloro dimer impurity is lower as the pH increases, however the actual amount of dimer (at higher pH levels) is difficult to determine as it is eluting with BM PEG Esters.

TABLE 8

Effect of pH on BM EE level

| Sample at 25° C. | T0 | T1 | T2 | T4 | T6 |
|---|---|---|---|---|---|
| pH 3.23 | 0.02% | 0.83% | 1.79% | 3.28% | 5.76% |
| pH 3.30 | ND | 0.10% | 0.21% | 0.40% | 0.61% |
| pH 3.37 | ND | 0.06% | 0.13% | 0.24% | 0.41% |
| pH 3.45 | ND | 0.05% | 0.10% | 0.18% | 0.28% |
| pH 3.57 | ND | 0.04% | 0.09% | 0.16% | 0.24% |
| pH 3.66 | ND | 0.04% | 0.08% | 0.14% | 0.22% |
| pH 3.78 | ND | 0.04% | 0.07% | 0.13% | 0.20% |

Table 8 illustrates that that with time the BM EE impurity is lower as the pH increases.

TABLE 9

Effect of pH on Total Impurity level

| Sample at 25° C. | T0 | T1 | T2 | T4 | T6 |
|---|---|---|---|---|---|
| pH 3.23 | 0.02 | 2.64% | 5.71% | 10.46% | 18.05% |
| pH 3.30 | ND | 0.36% | 0.78% | 1.53% | 2.19% |
| pH 3.37 | 0.01% | 0.29% | 0.61% | 1.17% | 1.70% |
| pH 3.45 | 0.04% | 0.31% | 0.65% | 1.17% | 1.57% |
| pH 3.57 | 0.05% | 0.35% | 0.73% | 1.34% | 1.80% |
| pH 3.66 | 0.06% | 0.43% | 0.86% | 1.53% | 2.25% |
| pH 3.78 | 0.06% | 0.49% | 1.08% | 1.91% | 2.75% |

Table 9 is comparing the total impurity percentage at all pH levels. The optimum pH range was 3.37-3.57.

TABLE 10A

Effect of pH on Impurity Levels at 5° C. (the impurity quantities are %, based on the standard bendamustine HCl)

| Sample at 5° C. with indicated pH | T0 BM DCE | T4 BM DCE | T6 BM DCE | T0 BM HP1 | T4 BM HP1 | T6 BM HP1 | T0 BM PEG Ethers | T4 BM PEG Ethers | T6 BM PEG Ethers |
|---|---|---|---|---|---|---|---|---|---|
| 3.23 | ND | 0.02 | 0.20 | ND | 0.01 | ND | ND | ND | ND |
| 3.30 | ND | 0.02 | 0.02 | ND | 0.02 | ND | ND | 0.01 | 0.01 |
| 3.37 | ND | 0.02 | 0.03 | 0.01 | 0.01 | ND | 0.01 | 0.01 | 0.02 |
| 3.45 | ND | 0.03 | 0.03 | 0.02 | 0.01 | ND | 0.02 | 0.01 | 0.03 |
| 3.57 | ND | 0.03 | 0.04 | 0.02 | 0.02 | 0.02 | 0.02 | 0.02 | 0.04 |
| 3.66 | ND | 0.04 | 0.06 | 0.03 | 0.02 | 0.02 | 0.03 | 0.03 | 0.05 |
| 3.78 | ND | 0.05 | 0.08 | 0.04 | 0.02 | 0.03 | 0.04 | 0.03 | 0.07 |

TABLE 10B

Effect of pH on Impurity Levels at 5° C. (the impurity quantities are %, based on the standard bendamustine HCl)

| Sample at 5° C. with indicated pH | T0 BM PEG Esters | T4 BM PEG Esters | T6 BM PEG Esters | T0 Tri-Cl Dimer | T4 Tri-Cl Dimer | T6 Tri-Cl Dimer | T0 BM EE | T4 BM EE | T6 BM EE |
|---|---|---|---|---|---|---|---|---|---|
| 3.23 | ND | 0.42 | 0.60 | ND | 0.03 | 0.04 | 0.02 | 0.24 | 0.37 |
| 3.30 | ND | 0.06 | 0.06 | ND | 0.01 | ND | ND | 0.03 | 0.04 |
| 3.37 | ND | 0.04 | 0.04 | ND | 0.01 | ND | ND | 0.02 | 0.03 |
| 3.45 | ND | 0.04 | 0.06 | ND | 0.01 | ND | ND | 0.02 | 0.02 |
| 3.57 | ND | 0.05 | 0.07 | ND | 0.02 | ND | ND | 0.02 | 0.02 |
| 3.66 | ND | 0.03 | 0.07 | ND | 0.02 | ND | ND | 0.01 | 0.02 |
| 3.78 | ND | 0.03 | 0.08 | ND | 0.03 | ND | ND | 0.03 | 0.02 |

Note, in Table 10B, "Tri-CI dimer" is BM Trichloro Dimer.

As shown in Tables 10A and 10B, at 5° C. from T0 to T6 months, a similar fashion was observed to the accelerated 25° C. data: The BM EE and BM PEG Esters impurity levels are high when the pH of the formulation is lower than 3.3.

The experiments in this Example 2 demonstrated that pH affected the impurity profile of a bendamustine HCl formulation containing a small molecule organic solvent, an organic polymeric compound solvent (with multiple hydroxy moieties), and water. Where the pH of the formulation was lower than 3.30, high levels of BM EE and BM PEG Ester impurities were observed over time. Where the pH of the formulation was higher than 3.66, high levels of BM PEG Ether impurities were observed overtime.

Example 3: Long Term Stability of Liquid Bendamustine Formulations at Refrigeration Temperatures A study was performed to assess the difference in stability profile (as indicated by assay and impurity levels) of a bendamustine formulation according to the present invention and BENDEKA™ (comprising the ingredients listed in Table 11 below) when stored long term at both 2° C. and 8° C.

TABLE 11

Product/Formulations Details

| Drug Product | Bendamustine Formulation A | | BENDEKA™ | |
|---|---|---|---|---|
| Formulation | API | 25 mg/mL | API | 25 mg/mL |
| | BHA | 1 mg/mL | MTG | 5 mg/mL |
| | AA | 23.7 mg/ml (3% v/V) | PG | 0.1 mL |
| | WFI | 30 mg/ml (3% v/V) | PEG400 | Qs. |
| | PEG400 | Qs. | NaOH** | AR pH 3.2-3.3* |
| | NaOH** | AR pH 3.4-3.6* | | |

Note on Table 11:
"API" is bendamustine HCl;
"BHA" is butylated hydroxyanisole;
"WFI" is Water for Injection;
"AA" is ethanol;
"AR" is "as required";
"MTG" is monothioglycerol;
"PG" is propylene glycol;
"Qs" is "quantity sufficient"; and
"PEG" is polyethylene glycol".
*Formulation in a 12.4% aqueous solution (v/v).
**NaOH is used to adjust pH.

All samples were stored at 2-8° C. prior to the study start and after study completion. The samples were tested for pH, assay and related substances. After four months storage at 2°

C. and 8° C., the pH of and related substances in the samples were tested. After ten months storage at 2° C. and 8° C., the physical state of the samples was observed and sample photos were taken. After 12 months storage at 2° C. and 8° C., samples were tested for description, pH, assay and related substances. The presence and the amount of related substances were determined by HPLC using the following parameters:

| Method Requirement | Description |
|---|---|
| Column | Phenomenex CuroSil-PFP, 150 × 4.6 mm, 5 μm (pentaflurophenyl USP L43 packing) |
| Column temperature | 30° C. |
| Sample temperature | 5° C. |
| Detector wavelength | 260 nm |
| Flow rate | 1.0 mL/minute |
| Injection volume | 10 μL |
| Mobile phase A | 0.06M ammonium formate in WFI (pH 3.2) |
| Mobile Phase B | Acetonitrile |

| | Time | A (%) | B (%) |
|---|---|---|---|
| Gradient | 0 | 90 | 10 |
| | 15 | 73 | 27 |
| | 40 | 66 | 34 |
| | 45 | 54 | 46 |
| | 47 | 48 | 52 |
| | 50 | 90 | 10 |
| | 60 | 90 | 10 |

| Run time | 60 minutes |
|---|---|
| Diluent | Methanol |
| Sample solution concentration | 2.0 mg/mL | additionally, there was minimal degradation with Bendamustine Formulation A over the 12 month study period at any temperature. BENDEKA™ degraded significantly over the 12 month study period and there was a vast difference in both assay and impurity levels between 2° C. and 8° C. temperatures. The most significant change was observed with the unknown impurities in BENDEKA™. These impurities are in the "esters" group, specifically propylene glycol ester and PEG esters, which form when bendamustine HCl reacts with the propylene glycol and the PEG 400 in BENDEKA™. Based on the studies described herein (as demonstrated Example 2 above), low pH promotes formation of esters, and this may be responsible for the high levels of the propylene glycol and PEG esters observed in BENDEKA™ when stored over time in this study.

Additionally, the product vials on storage at 2° C. and 8° C. were observed and photos were taken. The results demonstrated that Bendamustine Formulation A was a liquid at both 2° C. and 8° C., but BENDEKA™ was a solid at 2° C. and a liquid at 8° C.

The study in this Example 3 demonstrated that BENDEKA™ is a frozen solid at 2° C. and a liquid at 8° C. An additional issue is the vast difference in impurity levels for BENDEKA™ when stored at 2° C. and 8° C., with total impurities of 3.7% and 14.5% respectively. The BENDEKA™ sample which was stored in the stability chamber at 2-8° C. (typical temperature was 4-6° C.) had a total impurity levels of 6.7%, which was between that of the 2° C. and 8° C. BENDEKA™ samples. In contrast, Bendamustine Formulation A was a liquid at both 2° C. and 8° C. There was no significant difference in impurity levels in Bendamustine formulation A when stored at either 2° C. or

TABLE 12

Stability data

| Sample | Time Point | Storage Temperature | Description | pH | Assay | BM DCE (Δ T0) | BM HP1 (Δ T0) | BM TRI CL DIMER (Δ T0) | BM EE (Δ T0) | Major Unknown (Δ T0) | Total Impurities (Δ T0) |
|---|---|---|---|---|---|---|---|---|---|---|---|
| Bendamustine HCl injecttion PB100 | T0 | N/A | Not tested | 3.45 | 99.4% | <0.05% | <0.05% | ND | ND | ND | <0.05% |
| | T4 | 2° C. | Not tested | 3.48 | Not tested | <0.05% | <0.05% | ND | ND | <0.05% | <0.05% |
| | | 8° C. | Not tested | 3.47 | Not tested | <0.05% | <0.05% | ND | <0.05% | <0.05% | <0.05% |
| | T12 | 2° C. | Complies | 3.53 | 98.9% | <0.05% | <0.05% | <0.05% | <0.05% | <0.05% | <0.05% |
| | | 4-6° C.* | Complies | 3.52 | 98.7% | <0.05% | <0.05% | <0.05% | 0.05% | <0.05% | 0.05% |
| | | 8° C. | Complies | 3.52 | 98.4% | <0.05% | <0.05% | <0.05% | 0.06% | <0.05% | 0.06% |
| Bendeka™ ZBR049 | T0 | N/A | Not tested | 3.17 | 97.1% | 0.39% | 0.05% | NC | ND | 0.07% | 0.74% |
| | T4 | 2° C. | Not tested | 3.19 | Not tested | 0.39% | 0.06% | ND | <0.05% | 0.22% | 1.2% |
| | | 8° C. | Not tested | 3.19 | Not tested | 0.36% | 0.06% | ND | <0.05% | 0.30% | 1.6% |
| | T12 | 2° C. | Complies | 3.23 | 94.3% | 0.32% | 0.05% | <0.05% | ND | 0.92% | 3.7% |
| | | 4-6° C.* | Complies | 3.24 | 91.1% | 0.31% | 0.05% | <0.05% | ND | 1.67% | 6.7% |
| | | 8° C. | Complies | 3.23 | 82.7% | 0.36% | 0.05% | <0.05% | ND | 3.5% | 14.5% |

Description for Table 12: "Complies" was defined as a clear, colourless to yellow-coloured solution, practically free from visible particulates. ND=Not Detected. Reporting threshold is >0.05%. "Δ T0" refers to the change in the amount of the specified related substance from T0 to either four months later or twelve months later, as indicated, when stored at the indicated temperature or temperature range.

*Stored at 2-8° C., but chamber temperature was typically 4-6° C.

The results of this study show that both BENDEKA™ and Bendamustine Formulation A were clear and colorless-to-yellow after 12 months storage at 2° C. and 8° C. The stability of Bendamustine Formulation A after storage at either 2° C. or 8° C. for 12 months was comparable; 8° C., with total impurities of <0.05% and 0.06% respectively. Bendamustine Formulation A stored in the stability chamber at 2-8° C. (typical temperature was 4-6° C.) had total impurity levels of 0.05%.

PEG 400, a suitable solvent for bendamustine HCl, has a freezing point of approximately 4° C. The proposed long term storage temperature of a bendamustine drug product is refrigeration temperature (2-8° C.). Thus, if the bendamustine drug product formulation contains PEG 400, there is a possibility that freezing may occur during storage that may result in significant differences in impurity levels over the temperature range depending on whether the product is a liquid or a frozen solid. Additionally, having a frozen product is not end-user friendly, as it has to be warmed prior to administration. The study in this Example 3 shows that a bendamustine formulation of the present invention, Bendamustine Formulation A, avoids the problem of freezing when stored under standard refrigeration conditions.

Example 4: Organic Solvents

An initial study was performed to assess bendamustine HCl solubility and brief stability in various organic solvents. Amounts of approximately 415.4 mg bendamustine HCl API (active pharmaceutical ingredient) were weighed into 4 mL amber glass vials. 2 mL of each indicated test solvent was added to two of each of the vials. One of each set of two vials containing the same solvent was placed on a sample roller at 2-8° C., and the other vial in each set was placed on a sample roller at laboratory temperature overnight. The following day, the solution from each vial was filtered through a Pall, 0.2 μm Fluorodyne II (Hydrophilic modified PVDF) syringe filter into a fresh 4 mL amber glass vial.

The solubility of bendamustine HCl was given by the TO assay analysis, and the results are summarized in Table 13. The temperature in the laboratory was measured to be 23° C., thus solubility was determined at 2-8° C. and at 23° C. Mostly, bendamustine HCl solubility was found to be higher at 23° C. than at 2-8° C.

Benzyl alcohol, dimethyl sulfoxide, 1-methyl-2-pyrrolidinone and the dimethyl acetamide showed high bendamustine HCl solubility (>180 mg/mL). They all completely dissolved the API, at both temperatures tested, indicating bendamustine HCl solubility is approximately 180 mg/mL or above in these solvents.

Propylene glycol also had high bendamustine HCl solubility, giving approximately 155 mg/mL at 2-8° C. and 170 mg/mL at 23° C. Negligible differences were observed between three propylene glycol suppliers (Merck Sharp & Dohme Corp., a subsidiary of Merck & Co., Inc.; The Dow Chemical Company; and Croda International Plc).

The remaining solvents had bendamustine HCl solubility limits below the concentration of 90 mg/mL in TREANDA® Injection (i.e. the TREANDA® (bendamustine hydrochloride), injection, for intravenous use, solution product). Ethanol was approximately 50-60 mg/mL, PEG 300 approximately 60 mg/mL and PEG 400 approximately 30 mg/mL. Thus, ethanol, PEG 300 and PEG 400 would require co-solvent(s) to reach 90 mg/mL. Isopropyl alcohol was even lower with only approximately 5 mg/mL of bendamustine HCl dissolving.

TABLE 13

Solubility of Bendamustine HCl in Organic Solvents

| | 2-8° C. | | 23° C. | |
|---|---|---|---|---|
| Solvent | Solubility (mg/mL) | Complete dissolution? | Solubility (mg/mL) | Complete dissolution? |
| Absolute Ethanol | 52.1 | N | 61.1 | N |
| Benzyl alcohol | 176.9 | Y | 174.0 | Y |
| Dimethyl sulfoxide | 181.5 | Y | 181.3 | Y |
| Isopropyl alcohol | 4.5 | N | 6.7 | N |
| 1-methyl-2-pyrrolidinone | 181.3 | Y | 180.3 | Y |
| Dimethyl acetamide (high purity)-Finar | 177.6 | Y | 179.3 | Y |
| Dimethyl acetamide (EP)-Finar | 180.5 | Y | 174.2 | Y |
| Dimethyl acetamide (EP)-Panreac | 182.2 | Y | 179.7 | Y |
| PEG 300 | 60.2 | N | 64.5 | N |

TABLE 13-continued

Solubility of Bendamustine HCl in Organic Solvents

| | 2-8° C. | | 23° C. | |
|---|---|---|---|---|
| Solvent | Solubility (mg/mL) | Complete dissolution? | Solubility (mg/mL) | Complete dissolution? |
| PEG 400 | 32.8 | N | 34.4 | N |
| Propylene glycol (USP)-Merck | 158.7 | N | 172.3 | Y |
| Propylene glycol (USP)-Dow | 153.7 | N | 165.8 | Y |
| Propylene glycol (USP)-Croda | 153.8 | N | 170.3 | Y |

"USP" is "United States Pharmacopeia", meaning the substance has been determined to be pure according to the standards published by the United States Pharmacopeia.
"EP" is European Pharmacopeia
"PEG" is polyethylene glycol Example 5: Bendamustine HCl Injection Formulation "C"

Bendamustine HCl monohydrate was used to prepare a liquid bendamustine formulation suitable for injection, wherein each mL of the formulation contains the following ingredients in polyethylene glycol 400: 25 mg bendamustine HCl, 1 mg butylated hydroxyanisole, 23.7 mg dehydrated ethanol, 30 mg water, and sodium hydroxide as needed to adjust the pH to from about 3.4 to about 3.6. To adjust and calculate the pH, the composition is tested in a water solution at about 12.4% v/v, and sodium hydroxide was added, if needed, until a pH of from about 3.4 to about 3.6 was achieved. The liquid bendamustine HCl formulation was filled into amber glass vials to make the following single-dose or multiple-dose presentations of ready-to-dilute bendamustine HCl solution: 1 mL presentation (containing 25 mg bendamustine HCl), 4 mL presentation (containing 100 mg bendamustine HCl), and 8 mL presentation (containing 200 mg bendamustine HCl). These formulations maintained a pH target range of from about 3.3 to about 3.7 over the stability program.

Example 6: Bendamustine Formulations with Increasing Water Content

A study was performed to assess the effect of water content (10-30% v/v) on the stability of a Bendamustine HCl formulation. Formulations containing identical amounts of Bendamustine HCl, Butylated Hydroxy Anisole and Absolute alcohol but with increasing amounts of water were prepared as shown in the table below.

| FORMULATION (F) | 1 | 2 | 3 | 4 | 5 |
|---|---|---|---|---|---|
| Bendamustine HCl | 25 mg/mL | 25 mg/mL | 25 mg/mL | 25 mg/mL | 25 mg/mL |
| Butylated Hydroxy Anisole | 1 mg/mL | 1 mg/mL | 1 mg/mL | 1 mg/mL | 1 mg/mL |
| Absolute Alcohol | 3% v/V | 3% v/V | 3% v/V | 3% v/V | 3% v/V |
| Water | 10% v/V | 15% v/V | 20% v/V | 25% v/V | 30% v/V |
| PEG400 | Qs. to 1 mL | Qs. to 1 mL | Qs. to 1 mL | Qs. to 1 mL | Qs. to 1 mL |
| pH | Approx. 3.5 | Approx. 3.5 | Approx. 3.5 | Approx. 3.5 | Approx. 3.5 |

These formulations were placed on stability for 7 months at 2-8° C. and 25° C. Related substances testing was performed at the initial time point (0 M), after 1 month (1 M) and after 7 months (7M) storage. The results are shown in the Tables 14 and 15 below.

TABLE 14

| 2-8° C. STORAGE | BENDAMUSTINE DECHLOROETHYL IMPURITY | | | BENDAMUSTINE HYDROLYSIS PRODUCT 1 IMPURITY | | | BENDAMUSTINE TRI-CHLORO DIMER IMPURITY | | | BENDAMUSTINE ETHYL ESTER IMPURITY | | | MAJOR UNKNOWN IMPURITY | | | TOTAL IMPURITIES | | |
|---|---|---|---|---|---|---|---|---|---|---|---|---|---|---|---|---|---|---|
| Test Point | 0 M | 1 M | 7 M | 0 M | 1 M | 7 M | 0 M | 1 M | 7 M | 0 M | 1 M | 7 M | 0 M | 1 M | 7 M | 0 M | 1 M | 7 M |
| F1 -10% water | ND | ND | <QL | ND | ND | 0.07 | ND | ND | <QL | ND | ND | ND | ND | ND | ND | ND | ND | 0.1 |
| F2 -15% water | ND | ND | <QL | ND | <QL | 0.21 | ND | ND | 0.09 | ND | ND | ND | ND | ND | ND | ND | ND | 0.3 |
| F3 -20% water | ND | ND | <QL | ND | 0.09 | 0.55 | ND | <QL | 0.26 | ND | ND | ND | ND | ND | 0.05 | ND | ND | 0.9 |
| F4 -25% water | ND | ND | <QL | ND | 0.18 | 1.08 | ND | 0.10 | 0.57 | ND | ND | ND | ND | ND | 0.08 | ND | 0.28 | 1.8 |
| F5 -30% water | ND | ND | <QL | ND | 0.34 | 1.94 | ND | 0.21 | 1.11 | ND | ND | <QL | ND | ND | 0.1 | ND | 0.55 | 3.5 |

M = months;
ND = Not detected,
QL = Quantitation Limit

TABLE 15

| 25° C. STORAGE | BENDAMUSTINE DECHLOROETHYL IMPURITY | | | BENDAMUSTINE HYDROLYSIS PRODUCT 1 IMPURITY | | | BENDAMUSTINE TRI-CHLORO DIMER IMPURITY | | | BENDAMUSTINE ETHYL ESTER IMPURITY | | | MAJOR UNKNOWN IMPURITY | | | TOTAL IMPURITIES | | |
|---|---|---|---|---|---|---|---|---|---|---|---|---|---|---|---|---|---|---|
| Test Point | 0 M | 1 M | 7 M | 0M | 1 M | 7 M | 0 M | 1 M | 7 M | 0M | 1 M | 7 M | 0 M | 1 M | 7 M | 0 M | 1 M | 7 M |
| 10% water | ND | ND | 0.16 | ND | 0.17 | 1.02 | NC | 0.05 | 0.29 | ND | <QL | 0.22 | ND | <QL | 0.17 | ND | 0.2 | 3.3 |
| 15% water | ND | 0.07 | 0.31 | ND | 0.52 | 2.73 | ND | 0.15 | 0.66 | ND | <QL | 0.24 | ND | <QL | 0.23 | ND | 0.7 | 6.3 |
| 20% water | ND | ND | 0.21 | ND | 1.30 | 5.15 | ND | 0.41 | 1.09 | ND | <QL | 0.32 | ND | 0.09 | 0.29 | ND | 1.9 | 10.1 |
| 25% water | ND | ND | 0.18 | ND | 2.59 | 7.14 | ND | 0.83 | 1.26 | ND | <QL | 0.84 | ND | 0.13 | 0.45 | NC | 4.0 | 14.7 |
| 30% water | ND | ND | 0.47 | ND | 4.32 | 9.16 | ND | 1.34 | 1.12 | ND | <QL | 2.11 | ND | 0.15 | 1.03 | ND | 6.7 | 22.8 |

M = months;
ND = Not detected,
QL = Quantitation Limit

The invention claimed is:

1. A concentrated liquid pharmaceutical composition comprising a) 25 mg/mL of bendamustine hydrochloride b) 23.7 mg/mL of absolute ethanol, c) 1 mg/mL butylated hydroxyanisole, d) 30 mg/mL water for injection, and 4) polyethylene glycol 400 quantity sufficient, wherein the pharmaceutical composition is, after dilution, suitable for administration to a mammal by injection.

* * * * *